US012044686B2

(12) United States Patent
Yuan et al.

(10) Patent No.: US 12,044,686 B2
(45) Date of Patent: Jul. 23, 2024

(54) COMPOSITIONS AND METHODS FOR ASSAYING NEUTRALIZING ANTIBODIES

(71) Applicant: Diazyme Laboratories, Inc., Poway, CA (US)

(72) Inventors: Chong-Sheng Yuan, San Diego, CA (US); Fakhri B. Saida, San Diego, CA (US); Abhijit Datta, San Diego, CA (US); Chao Dou, San Diego, CA (US)

(73) Assignee: DIAZYME LABORATORIES, INC., Poway, CA (US)

( * ) Notice: Subject to any disclaimer, the term of this patent is extended or adjusted under 35 U.S.C. 154(b) by 221 days.

(21) Appl. No.: 17/376,058

(22) Filed: Jul. 14, 2021

(65) Prior Publication Data

US 2022/0018850 A1   Jan. 20, 2022

Related U.S. Application Data

(60) Provisional application No. 63/052,308, filed on Jul. 15, 2020.

(51) Int. Cl.
*G01N 33/543* (2006.01)
*G01N 33/68* (2006.01)

(52) U.S. Cl.
CPC ... *G01N 33/6854* (2013.01); *G01N 33/54326* (2013.01); *G01N 2333/165* (2013.01); *G01N 2333/948* (2013.01)

(58) Field of Classification Search
None
See application file for complete search history.

(56) References Cited

U.S. PATENT DOCUMENTS

| | | | |
|---|---|---|---|
| 11,054,429 B1 | 7/2021 | Wang | |
| 11,112,412 B1 | 9/2021 | Wang | |
| 2009/0291508 A1* | 11/2009 | Babu | B82Y 30/00 422/68.1 |
| 2012/0308997 A1 | 12/2012 | Ruan et al. | |
| 2017/0102401 A1* | 4/2017 | Trieu | C07K 16/44 |
| 2019/0195798 A1 | 6/2019 | Ruan et al. | |
| 2021/0302434 A1* | 9/2021 | Wang | G01N 33/56983 |
| 2021/0364508 A1* | 11/2021 | Wang | G01N 33/54306 |
| 2021/0389308 A1* | 12/2021 | Lapointe | C07K 14/005 |
| 2023/0091170 A1* | 3/2023 | Soldo | G01N 33/54313 435/7.1 |

FOREIGN PATENT DOCUMENTS

| | | | |
|---|---|---|---|
| EP | 3527987 A1 | 8/2019 | |
| EP | 3800473 A1 | 4/2021 | |
| GB | 0191640 | * 2/1986 | G01N 33/52 |

OTHER PUBLICATIONS

Rey et al., Personalized stress monitoring: a smart phone-enabled system for quantification of salivary control, Personal and Ubiquitous Computing, 2018, 22: pp. 867-877. (Year: 2018).*
Al-Lazikani et al., "Standard conformations for the canonical structures of immunoglobulins." Journal of molecular biology (1997) 273(4): 927-948.
Byrnes et al., "A SARS-CoV-2 serological assay to determine the presence of blocking antibodies that compete for human ACE2 binding." medRxiv. Retrieved on May 6, 2022. Retrieved from https://www.ncbi.nlm.nih.gov/pmc/articles/PMC7273274/.
Chothia et al., "Canonical structures for the hypervariable regions of immunoglobulins." Journal of molecular biology (1987) 196(4): 901-917.
Chothia et al., "Conformations of immunoglobulin hypervariable regions." Nature (1989) 342(6252): 877-83.
Chothia et al., "Domain association in immunoglobulin molecules: the packing of variable domains." Journal of molecular biology (1985) 186(3): 651-663.
Forster et al., "Phylogenetic network analysis of SARS-CoV-2 genomes." Proceedings of the National Academy of Sciences (2020) 117(17): 9241-9243.
Gniffke et al., "Plasma from recovered COVID-19 patients inhibits spike protein binding to ACE2 in a microsphere-based inhibition assay." The journal of infectious diseases (2020) 222(12):1965-73.
Greenberg et al., "A new antigen receptor gene family that undergoes rearrangement and extensive somatic diversification in sharks." Nature (1995) 374: 168-173.
Hamers-Casterman et al., "Naturally occurring antibodies devoid of light chains." Nature (1993) 363: 446-448.
Hassanzadeh-Ghassabeh et al., "Nanobodies and their potential applications. Nanomedicine." (2013) 8(6):1013-26.
Hoffmann et al., "SARS-CoV-2 cell entry depends on ACE2 and TMPRSS2 and is blocked by a clinically proven protease inhibitor." Cell (2020) 181(2): 271-280.
International Search Report and Written Opinion for PCT/US2021/041696, dated Jan. 17, 2022, 21 pages.
Invitation to Pay Additional Fees and Where Applicable, Protest Fees for PCT/US2021/041696, dated Jul. 14, 2021, 16 pages.
Kabat et al., "Identical V region amino acid sequences and segments of sequences in antibodies of different specificities. Relative contributions of VH and VL genes, minigenes, and complementarity-determining regions to binding of antibody-combining sites." The Journal of Immunology (1991) 147(5):1709-1719.
Kabat, "Nature of the Antibody Combining Site." In Antibodies (1987) 19-40. Springer, Boston, MA.
Kirchdoerfer et al., "Pre-fusion structure of a human coronavirus spike protein." Nature (2016) 531(7592): 118-121.
Li, "Structure, function, and evolution of coronavirus spike proteins." Annual review of virology (2016) 3:237-261.
Maier et al. Coronaviruses Britton. "Methods and protocols." *Methods in molecular biology* (2015): 1282, Chapter 15.
McEnroe et al., "Interference testing in clinical chemistry; approved guideline—second edition" Wayne, PA: CLSI; 2005.

(Continued)

*Primary Examiner* — Gary Counts
(74) *Attorney, Agent, or Firm* — KNOBBE, MARTENS, OLSON & BEAR LLP

(57) ABSTRACT

Provided herein are compositions and methods for analyzing neutralizing antibodies to SARS-CoV-2, for example, in a sample from a subject suspected of having, having, or having had (e.g., having recovered from) a SARS-CoV-2 infection, or a subject having received a prophylactic and/or therapeutic intervention for a coronavirus infection.

14 Claims, 8 Drawing Sheets

(56) References Cited

OTHER PUBLICATIONS

Muruato et al., "A high-throughput neutralizing antibody assay for COVID-19 diagnosis and vaccine evaluation." Nature communications (2020) 11(1):1-6.
NCBI accession No. NC_045512, "Severe acute respiratory syndrome coronavirus 2 isolate Wuhan-Hu-1, complete genome." Retrieved on May 6, 2022. Retrieved from https://www.ncbi.nlm.nih.gov/nuccore/NC_045512.2/.
Ravichandran et al., "Antibody signature induced by SARS-CoV-2 spike protein immunogens in rabbits." Science translational medicine (2020) 12(550):eabc3539.
Tholen et al., "Evaluation of the linearity of quantitative measurement procedures: a statistical approach; approved guideline." Wayne, PA: CLSI; 2003.
Walls et al., "Structure, function, and antigenicity of the SARS-CoV-2 spike glycoprotein." Cell (2020) 181(2): 281-292.
Zhou et al., "A pneumonia outbreak associated with a new coronavirus of probable bat origin." Nature (2020) 579(7798): 270-273.

* cited by examiner

COMPOSITIONS AND METHODS FOR ASSAYING NEUTRALIZING ANTIBODIES

CROSS-REFERENCE TO RELATED APPLICATION

This application claims priority from U.S. provisional application No. 63/052,308, filed Jul. 15, 2020, entitled "COMPOSITIONS AND METHODS FOR ASSAYING NEUTRALIZING ANTIBODIES," which is incorporated by reference in its entirety for all purposes.

FIELD

The present disclosure generally relates to the field of antibody detection. In particular, the present disclosure provides kits and methods for detecting neutralizing antibodies to a coronavirus, such as SARS-CoV-2, in a sample such as a biological fluid, including serum or plasma samples, from a subject suspected of having, having, or having had a coronavirus infection, or a subject having received a prophylactic and/or therapeutic intervention for a coronavirus infection.

BACKGROUND

Coronaviruses are enveloped, positive-sense single-stranded RNA viruses. Certain coronaviruses, including the Middle East respiratory syndrome coronavirus (MERS-CoV), the severe acute respiratory syndrome coronavirus (SARS-CoV-1), and the most recent 2019 new coronavirus (2019-nCoV), also known as SARS-CoV-2, are highly pathogenic. The high pathogenicity and airborne transmissibility of these coronaviruses have raised concern about the potential for another coronavirus pandemic. The high case-fatality rate, vaguely defined epidemiology, and lack of prophylactic or therapeutic measures against coronaviruses have created an urgent need for rapid, effective, and accurate methods for detecting infection. Provided are methods, uses and articles of manufacture that meet such and other needs.

BRIEF SUMMARY

In some aspects, the present disclosure provides methods and compositions, e.g., kits, for assaying SARS-CoV-2 neutralizing antibodies in a biological sample, such as human serum or plasma. Compared to ELISA or ELISA-based assays, the methods and compositions disclosed herein provide a more sensitive and rapid assay format that is easy to perform and compatible with commercial analyzers.

In some aspects, the present disclosure provides a series of reagents containing the SARS-CoV-2 Spike protein Receptor Binding Domain (RBD) conjugated to particles (magnetic or polystyrene) and the human Angiotensin-Converting Enzyme 2 (hACE2) conjugated to a chemiluminescent label such as Acridinium Ester (AE), N-(4-aminobutyl)-N-ethylisoluminol (ABEI), or Alkaline Phosphatase (AP) or to another polystyrene particle. In one embodiment, in the absence of SARS-CoV-2 neutralizing antibodies, hACE2 and RBD form immune-complexes that generate a chemiluminescent signal (measured in Relative Light Units, RLU). In the presence of SARS-CoV-2 neutralizing antibodies, e.g., originating from human serum or plasma (e.g., EDTA plasma and Li-Heparin plasma), the interaction between hACE2 and RBD is compromised and the chemiluminescent signal is reduced in a dose-dependent manner.

In another embodiment, in the absence of SARS-CoV-2 neutralizing antibodies, hACE2 and RBD form immune-complexes that generate an agglutination signal that can be measured spectrophotometrically. In the presence of SARS-CoV-2 neutralizing antibodies, originating from human serum or plasma, the interaction between hACE2 and RBD is compromised and the agglutination-based spectrophotometric signal is reduced in a dose-dependent manner. Kits and reaction mixtures for assaying SARS-CoV-2 neutralizing antibodies in a sample are also provided.

In some embodiments, disclosed herein is a neutralizing antibody test for a SARS-CoV-2 coronavirus. In some embodiments, the method comprises: (a) mixing a serum or plasma sample with magnetic particles coated with a spike protein of a receptor binding domain (RBD) of a SARS-CoV-2 virus, and with a solution containing a human ACE2 receptor labelled with a chemiluminescent signal generating molecule; (b) after incubation and/or a washing step, measuring a chemiluminescent signal (RLU) on magnetic particles. In some embodiments, the intensity of RLU is inversely proportional to the amount of a SARS-CoV-2 neutralizing antibody in the sample.

In some embodiments, disclosed herein is a neutralizing antibody test for SARS-CoV-2 coronavirus, comprising the steps of: (a) mixing a serum or plasma sample with magnetic particles coated with a spike proteins of a receptor binding domain (RBD) of a SARS-CoV-2 virus; (b) after incubation of (a) and a washing step, adding a solution containing a human ACE2 receptor labelled with a chemiluminescent signal generating molecule; (c) after incubation and a washing step, measuring a chemiluminescent signal (RLU) on magnetic particles. In some embodiments, the intensity of RLU is inversely proportional to the amount of a SARS-CoV-2 neutralizing antibody in the sample.

In some embodiments, disclosed herein is a neutralizing antibody test for SARS-CoV-2 coronavirus, comprising the steps of: (a) mixing a serum or plasma sample with magnetic particles coated with a human ACE2 receptor and with a solution containing a spike protein of a receptor binding domain (RBD) of a SARS-CoV-2 virus, wherein the spike protein is labelled with a chemiluminescent signal generating molecule; (b) after incubation and a washing step, measuring a chemiluminescent signal (RLU) on magnetic particles. In some embodiments, the intensity of RLU is inversely proportional to the amount of a SARS-CoV-2 neutralizing antibody in the sample.

In some embodiments, disclosed herein is a neutralizing antibody test for SARS-CoV-2 coronavirus, comprising the steps of: (a) mixing a serum or plasma sample with magnetic particles coated with a human ACE2 receptor; (b) after incubation of (a) and a washing step, adding a solution containing a spike protein of a receptor binding domain of a SARS-CoV-2 virus, wherein the spike protein is labelled with a chemiluminescent signal generating molecule; (c) after incubation and a washing step, measuring a chemiluminescent signal (RLU) on magnetic particles. In some embodiments, the intensity of RLU is inversely proportional to the amount of a SARS-CoV-2 neutralizing antibody in the sample.

In any of the preceding embodiments, the chemiluminescent signal generating molecule can be or comprise Acridinium Ester (AE), N-(4-aminobutyl)-N-ethylisoluminol (ABEI), Alkaline Phosphatase (AP), and/or Horseradish Peroxidase (HRP).

In some embodiments, disclosed herein is a homogeneous assay for detecting and/or analyzing an amount or level of a neutralizing antibody against SARS-CoV-2 coronavirus comprising the steps of (a) mixing a serum or plasma sample with a first solution comprising latex particles (Particles A) coated with a spike protein of a receptor binding domain (RBD) of a SARS-CoV-2 virus and a second solution comprising latex particles (Particles B) coated with a human ACE2 receptor, in any suitable order or at the same time; (b) after incubation, measuring a degree of particle agglutination spectrophotometrically, wherein the agglutination is inversely proportional to an amount or level of a SARS-CoV-2 neutralizing antibody in the sample.

In some embodiments, disclosed herein is a homogeneous assay for detecting and/or analyzing an amount or level of a neutralizing antibody against SARS-CoV-2 coronavirus comprising the steps of (a) mixing a serum or plasma sample with a reaction buffer (e.g., a diluent) followed by additions of, in any suitable order or at the same time, a first solution comprising latex particles (Particles A) coated with a spike protein of a receptor binding domain (RBD) of a SARS-CoV-2 virus and a second solution comprising latex particles (Particles B) coated with a human ACE2 receptor; (b) after incubation, measuring a degree of particle agglutination spectrophotometrically, wherein the agglutination is inversely proportional to an amount or level of a SARS-CoV-2 neutralizing antibody in the sample.

DETAILED DESCRIPTION

Figure 1:
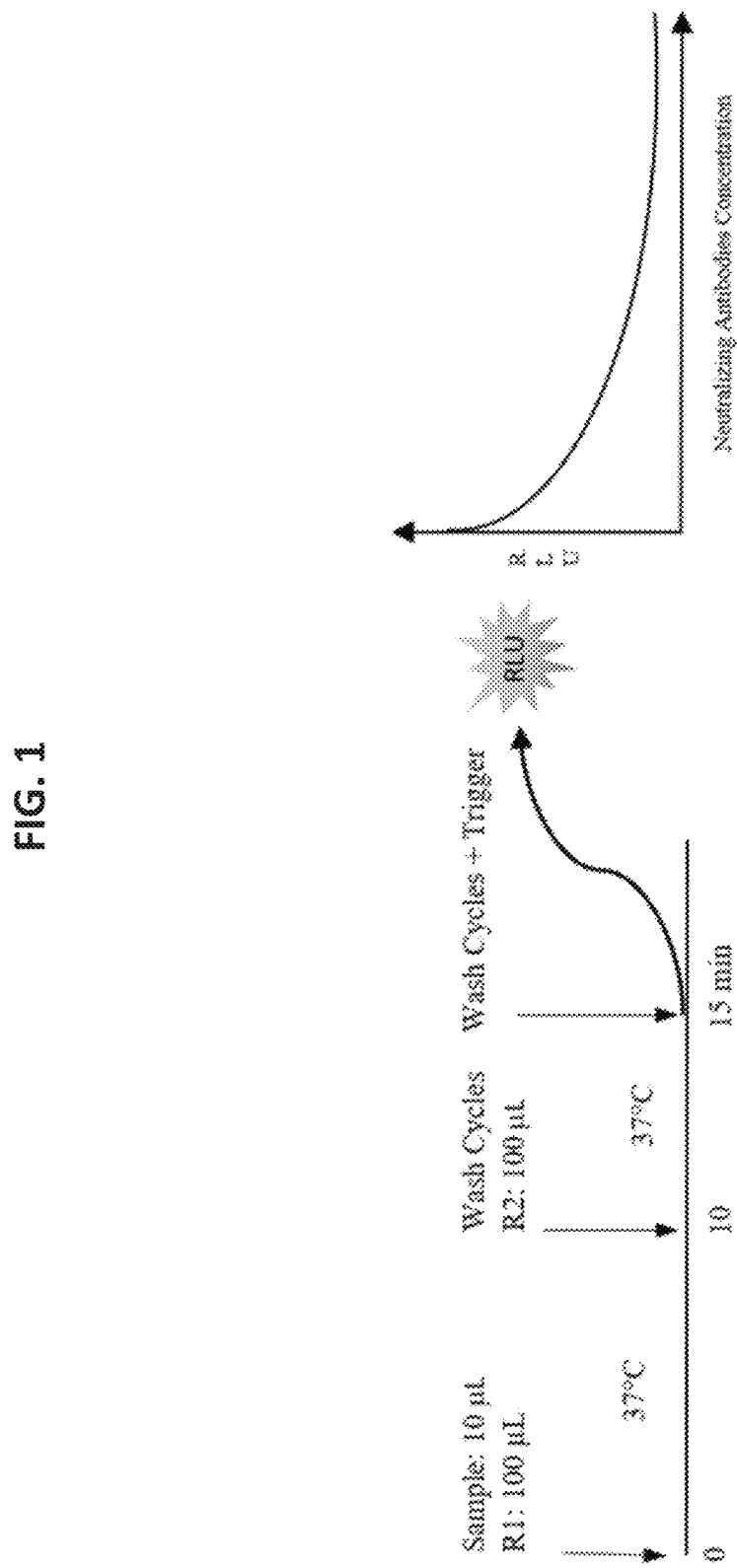
FIG. 1 shows an exemplary assay scheme utilizing coated magnetic beads.

In some aspects, provided herein is a neutralizing antibody test for a coronavirus, such as SARS-CoV-2. In some embodiments, provided herein is a method for detecting and/or analyzing one or more neutralizing antibodies, e.g., neutralizing antibodies to SARS-CoV-2.

In some aspects, provided herein are methods for detecting and/or analyzing one or more neutralizing antibodies, such as neutralizing antibodies to SARS-CoV-2, using particles (e.g., magnetic particles). The particle-based approach described herein provides multiple advantages over currently existing methods. Primarily, the particle-based approach allows for automation which negates the need for one or more or all manual pipetting steps. Additionally, the particle-based approach has increased sensitivity and greater ease of use over currently existing manual procedures (e.g. ELISA-based assays). The methods of the assay described herein mimic the in vivo virus-host interaction and vector-based neutralization assays (pVNT), which results in a faster and safer alternative to the traditional, low throughput, live virus cell-based assays for neutralizing antibodies.

In some embodiments, the methods described herein are conducted on a general chemistry analyzer or a clinical chemistry analyzer. In some embodiments, the analyzer can be obtained from, but not limited to, Roche, Hitachi, Modular P, Cobas series, Beckman/Olympus AU series, Beckman Synchron and DXC series, or Abbot Architect series. In a specific embodiment, the method is performed on a fully automated immunoassay chemiluminescent analyzer.

In some embodiments, the method comprises contacting a sample (e.g., a serum or plasma sample), a particle (e.g., magnetic particles) coated with a coronavirus antigen (e.g., the S protein of SARS-CoV-2, or a fragment, domain, antigenic sequence, or epitope thereof), and a receptor for the coronavirus antigen labelled with a signal generating molecule. Contacting of the three components may be performed in any suitable order or at the same time. In some embodiments, the method comprises contacting a serum or plasma (e.g., EDTA plasma and Li-Heparin plasma) sample, magnetic particles coated with an S protein or fragment, domain, antigenic sequence, or epitope thereof, e.g., the receptor binding domain (RBD) of SARS-CoV-2 virus S protein, and a solution containing the human ACE2 receptor labelled with a chemiluminescent signal generating molecule.

In some embodiments, the method further comprises, optionally after incubation and one or more optional washing steps, a step of measuring a signal on the particle, wherein the signal is from the signal generating molecule of the labelled receptor that binds to the coronavirus antigen coated on the particle. In some embodiments, the signal is a chemiluminescent signal (e.g., RLU) and the method further comprises measuring the RLU on magnetic particles.

In any of the preceding embodiments, the magnitude of the signal (e.g., the intensity of the RLU) can be inversely proportional to the amount or level of the neutralizing antibody in the sample.

In some embodiments, the method comprises contacting a sample (e.g., a serum or plasma sample) and a particle (e.g., magnetic particles) coated with a coronavirus antigen (e.g., the S protein of SARS-CoV-2, or a fragment, antigenic sequence, or epitope thereof). In some embodiments, the method comprises contacting a serum or plasma sample and magnetic particles coated with an S protein or fragment, domain, antigenic sequence, or epitope thereof, e.g., the receptor binding domain (RBD) of SARS-CoV-2 virus S protein. In some embodiments, the method further comprises an incubation step, e.g., wherein the coronavirus antigen is allowed to interact with one or more neutralizing antibodies, if present, in the sample. In some embodiments, following the incubation step, the method further comprises a washing step, e.g., wherein molecules that nonspecifically interact with the coronavirus antigen coated on the particle are washed off, and optionally removed from the reaction mix.

In some embodiments, following the optional incubation and/or washing step(s), the method further comprises contacting one or more antibodies immobilized on the particle (due to their specific binding to the coronavirus antigen) with a receptor for the coronavirus antigen labelled with a signal generating molecule. In some embodiments, the method comprises contacting a serum or plasma sample and magnetic particles coated with an S protein or fragment, domain, antigenic sequence, or epitope thereof, e.g., the receptor binding domain (RBD) of SARS-CoV-2 virus S protein, and after incubation and a washing step, contacting the resultant reaction mix (e.g., the reaction mix containing neutralizing antibodies immobilized on the particle) with a solution containing the human ACE2 receptor labelled with a chemiluminescent signal generating molecule. In some embodiments, the method further comprises, optionally after incubation and one or more optional washing steps, a step of measuring a signal on the particle, wherein the signal is from the signal generating molecule of the labelled receptor that binds to the coronavirus antigen coated on the particle. In some embodiments, the signal is a chemiluminescent signal (e.g., RLU) and the method further comprises measuring the RLU on magnetic particles. In any of the preceding embodiments, the magnitude of the signal (e.g., the intensity of the RLU) can be inversely proportional to the amount or level of the neutralizing antibody in the sample.

In some embodiments, the method comprises contacting a sample (e.g., a serum or plasma sample), a particle (e.g., magnetic particles) coated with a receptor or functional subunit or fragment thereof for a coronavirus antigen (e.g., the S protein of SARS-CoV-2, or a fragment, antigenic sequence, or epitope thereof), and the coronavirus antigen labelled with a signal generating molecule. Contacting of the three components may be performed in any suitable order or at the same time. In some embodiments, the method comprises contacting a serum or plasma sample, magnetic particles coated with the human ACE2 receptor, and a solution containing an S protein or fragment, domain, antigenic sequence, or epitope thereof (e.g., the receptor binding domain (RBD) of SARS-CoV-2 virus S protein) labelled with a chemiluminescent signal generating molecule.

In some embodiments, the method further comprises, optionally after incubation and one or more optional washing steps, a step of measuring a signal on the particle, wherein the signal is from the signal generating molecule of the labelled coronavirus antigen that binds to the receptor or functional subunit or fragment thereof coated on the particle. In some embodiments, the signal is a chemiluminescent signal (e.g., RLU) and the method further comprises measuring the RLU on magnetic particles.

In any of the preceding embodiments, the magnitude of the signal (e.g., the intensity of the RLU) can be inversely proportional to the amount or level of the neutralizing antibody in the sample.

In some embodiments, the method comprises contacting a sample (e.g., a serum or plasma sample) and a particle (e.g., magnetic particles) coated with a receptor or functional subunit or fragment thereof for a coronavirus antigen (e.g., the S protein of SARS-CoV-2, or a fragment, antigenic sequence, or epitope thereof). In some embodiments, the method comprises contacting a serum or plasma sample and magnetic particles coated with a receptor for an S protein or fragment, domain, antigenic sequence, or epitope thereof, e.g., the receptor binding domain (RBD) of SARS-CoV-2 virus S protein. In some embodiments, the method further comprises an incubation step, e.g., wherein the coronavirus antigen is allowed to interact with one or more neutralizing antibodies, if present, in the sample. In some embodiments, the mixture comprising the sample and the magnetic particles is precipitated in a magnetic field and the supernatant is decanted. In some embodiments, following the incubation step, the method further comprises a washing step, e.g., wherein molecules that nonspecifically interact with the receptor coated on the particle are washed off, and optionally removed from the reaction mix.

In some embodiments, following the optional incubation and/or washing step(s), the method further comprises contacting one or more antibodies immobilized on the particle (due to their specific binding to the receptor) with the coronavirus antigen labelled with a signal generating molecule. In some embodiments, the method comprises contacting a serum or plasma sample and magnetic particles coated with the human ACE2 receptor, and after incubation and a washing step, contacting the resultant reaction mix (e.g., the reaction mix containing neutralizing antibodies immobilized on the particle) with a solution containing an S protein or fragment, domain, antigenic sequence, or epitope thereof (e.g., the receptor binding domain (RBD) of SARS-CoV-2 virus S protein) labelled with a chemiluminescent signal generating molecule. In some embodiments, the method further comprises, optionally after incubation and one or more optional washing steps, a step of measuring a signal on the particle, wherein the signal is from the signal generating molecule of the labelled S protein or fragment, domain, antigenic sequence, or epitope thereof that binds to the receptor (e.g., hACE2) coated on the particle. In some embodiments, the signal is a chemiluminescent signal (e.g., RLU) and the method further comprises measuring the RLU on magnetic particles. In any of the preceding embodiments, the magnitude of the signal (e.g., the intensity of the RLU) can be inversely proportional to the amount or level of the neutralizing antibody in the sample.

In any of the preceding embodiments, the chemiluminescent signal generating molecules can comprise Acridinium Ester (AE), N-(4-aminobutyl)-N-ethylisoluminol (ABEI), Alkaline Phosphatase (AP), and/or Horseradish Peroxidase (HRP).

In some aspects, disclosed herein are homogenous assays for detecting and/or analyzing one or more neutralizing antibodies. In some embodiments, disclosed herein is a method for detecting an amount or level of a neutralizing antibody against the SARS-CoV-2 coronavirus.

In some embodiments, the method comprises contacting a sample (e.g., a serum or plasma sample) with a first solution comprising latex particles A coated with a coronavirus antigen (e.g., the S protein of SARS-CoV-2, or a fragment, antigenic sequence, or epitope thereof, such as an RBD of the S protein, or a fragment, antigenic sequence, or epitope of the RBD), and with a second solution comprising latex particles B coated with a receptor for the coronavirus antigen, e.g., a human ACE2 receptor or functional subunit or fragment thereof. Contacting among the sample, the first solution, the second solution, and optionally a diluent can occur simultaneously or sequentially in any suitable order or at the same time. An intermediate reaction mix comprising any two or more of the sample, the first solution, the second solution, and optionally a diluent, as well as a final reaction mix comprising all three of the sample and the first and second solutions (and optionally a diluent), may be formed. In some embodiments, the method further comprises incubating any one or more of the intermediate reaction mix(es) or the final reaction mix. In some embodiments, the method further comprises detecting and/or measuring the degree of particle agglutination, e.g., spectrophotometrically, e.g., in the final reaction mix. In any of the preceding embodiments, the degree of particle agglutination can be inversely proportional to an amount or level of one or more neutralizing antibodies in the sample.

In some embodiments, the method comprises contacting a sample (e.g., a serum or plasma sample) with a first solution comprising latex particles A coated with a coronavirus antigen (e.g., the S protein of SARS-CoV-2, or a fragment, antigenic sequence, or epitope thereof). In some embodiments, the coronavirus antigen is an RBD of the S protein, or a fragment, antigenic sequence, or epitope of the RBD. In some embodiments, the method further comprises mixing the reaction mix (e.g., a reaction mix comprising the sample mixed with the first solution) with a second solution comprising latex particles B coated with a receptor for the coronavirus antigen, e.g., a human ACE2 receptor or functional subunit or fragment thereof. In some embodiments, the method further comprises incubating a reaction mix comprising the sample mixed with the first solution and then the second solution. In some embodiments, the method further comprises detecting and/or measuring the degree of particle agglutination, e.g., spectrophotometrically. In any of the preceding embodiments, the degree of particle agglutination can be inversely proportional to an amount or level of one or more neutralizing antibodies in the sample.

In some embodiments, the method comprises contacting a sample (e.g., a serum or plasma sample) with a second solution comprising latex particles B coated with a receptor for a coronavirus antigen, e.g., a human ACE2 receptor or functional subunit or fragment thereof. In some embodiments, the method further comprises mixing the reaction mix (e.g., a reaction mix comprising the sample mixed with the second solution) with a first solution comprising latex particles A coated with a coronavirus antigen (e.g., the S protein of SARS-CoV-2, or a fragment, antigenic sequence, or epitope thereof). In some embodiments, the coronavirus antigen is an RBD of the S protein, or a fragment, antigenic sequence, or epitope of the RBD. In some embodiments, the method further comprises incubating a reaction mix comprising the sample mixed with the second solution and then the first solution. In some embodiments, the method further comprises detecting and/or measuring the degree of particle agglutination, e.g., spectrophotometrically. In any of the preceding embodiments, the degree of particle agglutination can be inversely proportional to an amount or level of one or more neutralizing antibodies in the sample.

In some embodiments, the method comprises contacting a sample (e.g., a serum or plasma sample) with a reaction buffer, e.g., a diluent. In some embodiments, the method further comprises contacting the sample mixed with the reaction buffer with a first solution and a second solution in any suitable order or at the same time. In some embodiments, the first solution comprises latex particles A coated with a coronavirus antigen (e.g., the S protein of SARS-CoV-2, or a fragment, antigenic sequence, or epitope thereof, such as an RBD of the S protein, or a fragment, antigenic sequence, or epitope of the RBD). In some embodiments, the second solution comprises latex particles B coated with a receptor for the coronavirus antigen, e.g., a human ACE2 receptor or functional subunit or fragment thereof. In some embodiments, the method further comprises incubating a reaction mix comprising the sample mixed with the first and second solutions. In some embodiments, the method further comprises detecting and/or measuring the degree of particle agglutination, e.g., spectrophotometrically. In any of the preceding embodiments, the degree of particle agglutination can be inversely proportional to an amount or level of one or more neutralizing antibodies in the sample.

In some embodiments, the coronavirus spike protein or fragment thereof is capable of binding to an antibody specific for a spike protein of a virulent coronavirus, such as SARS, SARS-CoV-2, MERS, hCoV-NL63, hCoV-229E, and HCoV-OC43. In some embodiments, the coronavirus spike protein or fragment thereof is capable of binding to an antibody specific for a spike protein of SARS-CoV-2. In some embodiments, the coronavirus spike protein or fragment thereof is capable of binding to antibodies that can recognize two or more isolates or clusters of SARS-CoV-2 (e.g., cluster A, B or C; or any one of the isolates in Table 1A or Table 1B). Antibodies contemplated herein include, but are not limited to, IgM, IgG, IgA, IgD, IgE and B cell receptor (BCR). In some embodiments, the coronavirus spike protein or fragment thereof is capable of binding to an antibody specific for a spike protein of a virulent coronavirus located on the surface of a B cell, such as a BCR on a B cell. In some embodiments, the coronavirus spike protein or fragment thereof is capable of binding to a secreted antibody, such as an antibody bound to an FcR on a host cell. In some embodiment, the antibody is a neutralizing antibody for a virulent coronavirus.

TABLE 1A

SARS-CoV-2 viral genome variants and their phylogenetic cluster assignment

| Type/Cluster | subtype | GISAID genome label | GISAID Accession ID | Collection date |
|---|---|---|---|---|
| B | derived | 4 BetaCov/Wuhan/IPBCAMS-WH-01/2019 | EPI_ISL_402123 | Dec. 24, 2019 |
| B | derived | 48 BetaCov/Wuhan/WH01/2019 | EPI_ISL_406798 | Dec. 26, 2019 |
| B | ancestral | 1 BetaCov/Wuhan/IVDC-HB-01/2019 | EPI_ISL_402119 | Dec. 30, 2019 |
| B | derived | 10 BetaCov/Wuhan/WIV05/2019 | EPI_ISL_402128 | Dec. 30, 2019 |
| B | ancestral | 11 BetaCov/Wuhan/WIV06/2019 | EPI_ISL_402129 | Dec. 30, 2019 |
| B | derived | 12 BetaCov/Wuhan/WIV07/2019 | EPI_ISL_402130 | Dec. 30, 2019 |
| B | derived | 19 BetaCov/Wuhan/IPBCAMS-WH-03/2019 | EPI_ISL_403930 | Dec. 30, 2019 |
| B | derived | 2 BetaCov/Wuhan/IVDC-HB-05/2019 | EPI_ISL_402121 | Dec. 30, 2019 |
| B | derived | 20 BetaCov/Wuhan/HBCDC-HB-01/2019 | EPI_ISL_402132 | Dec. 30, 2019 |
| B | derived | 250 BetaCov/Wuhan/HBCDC-HB-02/2019 | EPI_ISL_412898 | Dec. 30, 2019 |
| B | ancestral | 251 BetaCov/Wuhan/HBCDC-HB-03/2019 | EPI_ISL_412899 | Dec. 30, 2019 |
| B | ancestral | 5 BetaCov/Wuhan/WIV04/2019 | EPI_ISL_402124 | Dec. 30, 2019 |
| B | derived | 82 BetaCov/Wuhan/IPBCAMS-WH-02/2019 | EPI_ISL_403931 | Dec. 30, 2019 |
| B | ancestral | 83 BetaCov/Wuhan/IPBCAMS-WH-04/2019 | EPI_ISL_403929 | Dec. 30, 2019 |
| B | derived | 9 BetaCov/Wuhan/WIV02/2019 | EPI_ISL_402127 | Dec. 30, 2019 |
| B | ancestral | 110 BetaCov/Wuhan-Hu-1/2019 | EPI_ISL_402125 | Dec. 31, 2019 |
| B | derived | 3 BetaCov/Wuhan/IVDC-HB-04/2020 | EPI_ISL_402120 | Jan. 1, 2020 |

TABLE 1A-continued

SARS-CoV-2 viral genome variants and their phylogenetic cluster assignment

| Type/ Cluster | subtype | GISAID genome label | GISAID Accession ID | Collection date |
|---|---|---|---|---|
| B | ancestral | 49 BetaCov/Wuhan/WH03/2020 | EPI_ISL_406800 | Jan. 1, 2020 |
| B | ancestral | 75 BetaCov/Wuhan/IVDC-HB-envF13-20/2020 | EPI_ISL_408514 | Jan. 1, 2020 |
| B | derived | 76 BetaCov/Wuhan/IVDC-HB-envF13-21/2020 | EPI_ISL_408515 | Jan. 1, 2020 |
| B | derived | 84 BetaCov/Wuhan/IPBCAMS-WH-05/2020 | EPI_ISL_403928 | Jan. 1, 2020 |
| B | ancestral | 46 BetaCov/China/WHU01/2020 | EPI_ISL_406716 | Jan. 2, 2020 |
| B | ancestral | 47 BetaCov/China/WHU02/2020 | EPI_ISL_406717 | Jan. 2, 2020 |
| A | 29095C | 50 BetaCov/Wuhan/WH04/2020 | EPI_ISL_406801 | Jan. 5, 2020 |
| B | derived | 176 BetaCov/China/WH-09/2020 | EPI_ISL_411957 | Jan. 8, 2020 |
| B | derived | 224 BetaCov/Jingzhou/HBCDC-HB-01/2020 | EPI_ISL_412459 | Jan. 8, 2020 |
| B | ancestral | 7 BetaCov/Nonthaburi/61/2020 | EPI_ISL_403962 | Jan. 8, 2020 |
| A | 29095T | 28 BetaCov/Shenzhen/HKU-SZ-002/2020 | EPI_ISL_406030 | Jan. 10, 2020 |
| A | 29095T | 27 BetaCov/Shenzhen/HKU-SZ-005/2020 | EPI_ISL_405839 | Jan. 11, 2020 |
| B | derived | 72 BetaCov/Jiangxi/IVDC-JX-002/2020 | EPI_ISL_408486 | Jan. 11, 2020 |
| B | derived | 111 BetaCov/Nepal/61/2020 | EPI_ISL_410301 | Jan. 13, 2020 |
| A | 29095T | 40 BetaCov/Shenzhen/SZTH-002/2020 | EPI_ISL_406593 | Jan. 13, 2020 |
| B | ancestral | 8 BetaCov/Nonthaburi/74/2020 | EPI_ISL_403963 | Jan. 13, 2020 |
| A | 29095T | 13 BetaCov/Guangdong/20SF012/2020 | EPI_ISL_403932 | Jan. 14, 2020 |
| A | 29095T | 14 BetaCov/Guangdong/20SF013/2020 | EPI_ISL_403933 | Jan. 15, 2020 |
| B | derived | 15 BetaCov/Guangdong/20SF014/2020 | EPI_ISL_403934 | Jan. 15, 2020 |
| A | 29095T | 16 BetaCov/Guangdong/20SF025/2020 | EPI_ISL_403935 | Jan. 15, 2020 |
| A | 29095C | 71 BetaCov/Sichuan/IVDC-SC-001/2020 | EPI_ISL_408484 | Jan. 15, 2020 |
| B | derived | 21 BetaCov/Zhejiang/WZ-01/2020 | EPI_ISL_404227 | Jan. 16, 2020 |
| B | derived | 41 BetaCov/Shenzhen/SZTH-003/2020 | EPI_ISL_406594 | Jan. 16, 2020 |
| B | derived | 86 BetaCov/Shenzhen/SZTH-004/2020 | EPI_ISL_406595 | Jan. 16, 2020 |
| B | derived | 17 BetaCov/Guangdong/20SF028/2020 | EPI_ISL_403936 | Jan. 17, 2020 |
| B | ancestral | 22 BetaCov/Zhejiang/WZ-02/2020 | EPI_ISL_404228 | Jan. 17, 2020 |
| B | ancestral | 23 BetaCov/Zhejiang/WZ-02/2020 | EPI_ISL_404228 | Jan. 17, 2020 |
| A | 29095C | 266 BetaCov/Wuhan/HBCDC-HB-02/2020 | EPI_ISL_412978 | Jan. 17, 2020 |
| A | 29095C | 68 BetaCov/Yu--an/IVDC-YN-003/2020 | EPI_ISL_408480 | Jan. 17, 2020 |
| B | derived | 18 BetaCov/Guangdong/20SF040/2020 | EPI_ISL_403937 | Jan. 18, 2020 |
| A | 29095C | 267 BetaCov/Wuhan/HBCDC-HB-03/2020 | EPI_ISL_412979 | Jan. 18, 2020 |
| A | 29095C | 268 BetaCov/Wuhan/HBCDC-HB-04/2020 | EPI_ISL_412980 | Jan. 18, 2020 |
| B | derived | 269 BetaCov/Wuhan/HBCDC-HB-05/2020 | EPI_ISL_412981 | Jan. 18, 2020 |
| B | derived | 69 BetaCov/Chongqing/IVDC-CQ-001/2020 | EPIvISL_408481 | Jan. 18, 2020 |
| A | 29095C | 98 BetaCov/Beijing/IVDC-BJ-005/2020 | EPI_ISL_408485 | Jan. 18, 2020 |
| A | 29095C | 25 BetaCov/USA/WA1/2020 | EPI_ISL_404895 | Jan. 19, 2020 |
| B | ancestral | 57 BetaCov/Hangzhou/HZCDC0001/2020 | EPI_ISL_407313 | Jan. 19, 2020 |
| B | derived | 70 BetaCov/Shandong/IVDC-SD-001/2020 | EPI_ISL_408482 | Jan. 19, 2020 |
| B | ancestral | 73 BetaCov/Jiangsu/IVDC-JS-001/2020 | EPI_ISL_408488 | Jan. 19, 2020 |
| B | ancestral | 52 BetaCov/Hangzhou/HZ-1/2020 | EPI_ISL_406970 | Jan. 20, 2020 |
| A | 29095C | 157 BetaCov/Fujian/8/2020 | EPI_ISL_411060 | Jan. 21, 2020 |
| A | 29095C | 93 BetaCov/Chongqing/YC01/2020 | EPI_ISL_408478 | Jan. 21, 2020 |
| B | derived | 158 BetaCov/Fujian/13/2020 | EPI_ISL_411066 | Jan. 22, 2020 |
| A | 29095C | 189 BetaCov/Hong Kong/VM20001061/2020 | EPI_ISL_412028 | Jan. 22, 2020 |
| C | | 31 BetaCov/USA/CA2/2020 | EPI_ISL_406036 | Jan. 22, 2020 |
| A | 29095T | 32 BetaCov/USA/AZ1/2020 | EPI_ISL_406223 | Jan. 22, 2020 |
| B | derived | 33 BetaCov/Guangdong/20SF174/2020 | EPI_ISL_406531 | Jan. 22, 2020 |
| B | derived | 34 BetaCov/Guangzhou/20SF206/2020 | EPI_ISL_406533 | Jan. 22, 2020 |
| B | derived | 35 BetaCov/Foshan/20SF207/2020 | EPI_ISL_406534 | Jan. 22, 2020 |
| B | derived | 36 BetaCov/Foshan/20SF210/2020 | EPI_ISL_406535 | Jan. 22, 2020 |
| B | derived | 37 BetaCov/Foshan/20SF211/2020 | EPI_ISL_406536 | Jan. 22, 2020 |
| B | ancestral | 130 BetaCov/Japan/OS-20-07-1/2020 | EPI_ISL_410532 | Jan. 23, 2020 |
| C | | 154 BetaCov/France/IDF0372-is1/2020 | EPI_ISL_410720 | Jan. 23, 2020 |
| B | derived | 168 BetaCov/Jiangsu/S01/2020 | EPI_ISL_411950 | Jan. 23, 2020 |
| B | derived | 272 BetaCov/Canada/ON/VIDO-01/2020 | EPI_ISL_413015 | Jan. 23, 2020 |
| A | 29095C | 30 BetaCov/USA/CA1/2020 | EPI_ISL_406034 | Jan. 23, 2020 |
| B | ancestral | 38 BetaCov/Guangdong/20SF201/2020 | EPI_ISL_406538 | Jan. 23, 2020 |
| C | | 42 BetaCov/France/IDF0373/2020 | EPI_ISL_406597 | Jan. 23, 2020 |
| C | | 43 BetaCov/France/IDF0372/2020 | EPI_ISL_406596 | Jan. 23, 2020 |
| B | derived | 53 BetaCov/Singapore/1/2020 | EPI_ISL_406973 | Jan. 23, 2020 |
| C | | 87 BetaCov/Taiwan/2/2020 | EPI_ISL_406031 | Jan. 23, 2020 |
| B | ancestral | 94 BetaCov/Chongqing/ZX01/2020 | EPI_ISL_408479 | Jan. 23, 2020 |
| A | 29095C | 164 BetaCov/Taiwan/3/2020 | EPI_ISL_411926 | Jan. 24, 2020 |
| B | ancestral | 169 BetaCov/Jiangsu/S03/2020 | EPI_ISL_411953 | Jan. 24, 2020 |
| B | derived | 170 BetaCov/Jiangsu/S02/2020 | EPI_ISL_411952 | Jan. 24, 2020 |
| A | 29095C | 210 BetaCov/Vietnam/VR03-38142/2020 | EPI_ISL_408668 | Jan. 24, 2020 |
| A | 29095C | 58 BetaCov/Australia/NSW01/2020 | EPI_ISL_407893 | Jan. 24, 2020 |
| B | ancestral | 131 BetaCov/Japan/NA-20-05-1/2020 | EPI_ISL_410531 | Jan. 25, 2020 |
| A | 29095C | 135 BetaCov/USA/WA1-F6/2020 | EPI_ISL_407215 | Jan. 25, 2020 |
| B | ancestral | 163 BetaCov/Taiwan/CGMH-CGU-01/2020 | EPI_ISL_411915 | Jan. 25, 2020 |
| A | 29095C | 167 BetaCov/South Korea/KCDC03/2020 | EPI_ISL_407193 | Jan. 25, 2020 |
| B | derived | 274 BetaCov/Canada/ON-PHL2445/2020 | EPI_ISL_413014 | Jan. 25, 2020 |
| C | | 45 BetaCov/Australia/VIC01/2020 | EPI_ISL_406844 | Jan. 25, 2020 |

TABLE 1A-continued

SARS-CoV-2 viral genome variants and their phylogenetic cluster assignment

| Type/Cluster | subtype | GISAID genome label | GISAID Accession ID | Collection date |
|---|---|---|---|---|
| A | 29095C | 56 BetaCov/USA/WA1-A12/2020 | EPI_ISL_407214 | Jan. 25, 2020 |
| B | derived | 61 BetaCov/Singapore/2/2020 | EPI_ISL_407987 | Jan. 25, 2020 |
| B | derived | 81 BetaCov/Japan/AI/I-004/2020 | EPI_ISL_407084 | Jan. 25, 2020 |
| C | | 89 BetaCov/Sydney/3/2020 | EPI_ISL_408977 | Jan. 25, 2020 |
| C | | 145 BetaCov/Singapore/7/2020 | EPI_ISL_410713 | Jan. 27, 2020 |
| B | derived | 162 BetaCov/Cambodia/0012/2020 | EPI_ISL_411902 | Jan. 27, 2020 |
| B | derived | 91 BetaCov/USA/CA6/2020 | EPI_ISL_410044 | Jan. 27, 2020 |
| A | 29095C | 147 BetaCov/Australia/QLD01/2020 | EPI_ISL_407894 | Jan. 28, 2020 |
| C | | 160 BetaCov/France/IDF0386-is1P1/2020 | EPI_ISL_411219 | Jan. 28, 2020 |
| C | | 161 BetaCov/France/IDF0386-is1P3/2020 | EPI_ISL_411220 | Jan. 28, 2020 |
| B | ancestral | 165 BetaCov/Taiwan/4/2020 | EPI_ISL_411927 | Jan. 28, 2020 |
| B | derived | 44 BetaCov/Germany/BavPat1/2020 | EPI_ISL_406862 | Jan. 28, 2020 |
| A | 29095C | 90 BetaCov/USA/IL2/2020 | EPI_ISL_410045 | Jan. 28, 2020 |
| C | | 152 BetaCov/Italy/INMI1-is1/2020 | EPI_ISL_410545 | Jan. 29, 2020 |
| B | derived | 155 BetaCov/France/IDF0515-is1/2020 | EPI_ISL_410984 | Jan. 29, 2020 |
| B | derived | 257 BetaCov/China/IQTC02/2020 | EPI_ISL_412967 | Jan. 29, 2020 |
| C | | 264 BetaCov/Italy/SPL1/2020 | EPI_ISL_412974 | Jan. 29, 2020 |
| A | 29095C | 54 BetaCov/England/02/2020 | EPI_ISL_407073 | Jan. 29, 2020 |
| A | 29095C | 55 BetaCov/England/01/2020 | EPI_ISL_407071 | Jan. 29, 2020 |
| B | derived | 62 BetaCov/USA/CA5/2020 | EPI_ISL_408010 | Jan. 29, 2020 |
| B | derived | 63 BetaCov/USA/CA4/2020 | EPI_ISL_408009 | Jan. 29, 2020 |
| B | derived | 65 BetaCov/USA/CA3/2020 | EPI_ISL_408008 | Jan. 29, 2020 |
| B | derived | 66 BetaCov/France/IDF0515/2020 | EPI_ISL_408430 | Jan. 29, 2020 |
| B | derived | 67 BetaCov/France/IDF0626/2020 | EPI_ISL_408431 | Jan. 29, 2020 |
| A | 29095T | 77 BetaCov/Japan/TY-WK-012/2020 | EPI_ISL_408665 | Jan. 29, 2020 |
| B | derived | 80 BetaCovaapan/KY-V-029/2020 | EPI_ISL_408669 | Jan. 29, 2020 |
| B | derived | 92 BetaCov/USA/MA1/2020 | EPI_ISL_409067 | Jan. 29, 2020 |
| A | 29095C | 148 BetaCov/Australia/QLD02/2020 | EPI_ISL_407896 | Jan. 30, 2020 |
| C | | 190 BetaCov/Hong Kong/VM20001988/2020 | EPI_ISL_412029 | Jan. 30, 2020 |
| A | 29095C | 228 BetaCov/Korea/KCDC05/2020 | EPI_ISL_412869 | Jan. 30, 2020 |
| A | 29095C | 229 BetaCov/Korea/KCDC06/2020 | EPI_ISL_412870 | Jan. 30, 2020 |
| C | | 153 BetaCov/Italy/INMI1-cs/2020 | EPI_ISL_410546 | Jan. 31, 2020 |
| A | 29095C | 230 BetaCov/Korea/KCDC07/2020 | EPI_ISL_412871 | Jan. 31, 2020 |
| A | 29095T | 78 BetaCov/Japan/TY-WK-501/2020 | EPI_ISL_408666 | Jan. 31, 2020 |
| A | 29095T | 79 BetaCov/Japan/TY-WK-521/2020 | EPI_ISL_408667 | Jan. 31, 2020 |
| B | derived | 85 BetaCov/USA/WI1/2020 | EPI_ISL_408670 | Jan. 31, 2020 |
| B | derived | 191 BetaCov/Hong Kong/VB20026565/2020 | EPI_ISL_412030 | Feb. 1, 2020 |
| B | ancestral | 231 BetaCov/Korea/KCDC12/2020 | EPI_ISL_412872 | Feb. 1, 2020 |
| B | derived | 60 BetaCov/Singapore/3/2020 | EPI_ISL_407988 | Feb. 1, 2020 |
| B | derived | 151 BetaCov/Singapore/11/2020 | EPI_ISL_410719 | Feb. 2, 2020 |
| B | derived | 159 BetaCov/France/IDF0571/2020 | EPI_ISL_411218 | Feb. 2, 2020 |
| C | | 149 BetaCov/Singapore/8/2020 | EPI_ISL_410714 | Feb. 3, 2020 |
| A | 29095C | 59 BetaCov/Belgium/GHB-03021/2020 | EPI_ISL_407976 | Feb. 3, 2020 |
| C | | 146 BetaCov/Singapore/10/2020 | EPI_ISL_410716 | Feb. 4, 2020 |
| C | | 150 BetaCov/Singapore/9/2020 | EPI_ISL_410715 | Feb. 4, 2020 |
| A | 29095C | 143 BetaCov/Australia/QLD03/2020 | EPI_ISL_410717 | Feb. 5, 2020 |
| A | 29095C | 144 BetaCov/Australia/QLD04/2020 | EPI_ISL_410718 | Feb. 5, 2020 |
| B | derived | 256 BetaCov/China/IQTC01/2020 | EPI_ISL_412966 | Feb. 5, 2020 |
| B | derived | 95 BetaCov/Taiwan/NTU02/2020 | EPI_ISL_410218 | Feb. 5, 2020 |
| C | | 134 BetaCov/Singapore/5/2020 | EPI_ISL_410536 | Feb. 6, 2020 |
| A | 29095C | 172 BetaCov/USA/CA7/2020 | EPI_ISL_411954 | Feb. 6, 2020 |
| A | 29095C | 232 BetaCov/Korea/KCDC24/2020 | EPI_ISL_412873 | Feb. 6, 2020 |
| C | | 175 BetaCov/Sweden/01/2020 | EPI_ISL_411951 | Feb. 7, 2020 |
| A | 29095C | 270 BetaCov/Wuhan/HBCDC-HB-06/2020 | EPI_ISL_412982 | Feb. 7, 2020 |
| B | derived | 133 BetaCov/Singapore/6/2020 | EPI_ISL_410537 | Feb. 9, 2020 |
| C | | 212 BetaCov/England/03/2020 | EPI_ISL_412116 | Feb. 9, 2020 |
| C | | 226 BetaCov/England/09c/2020 | EPI_ISL_412116 | Feb. 9, 2020 |
| B | derived | 173 BetaCov/USA/CA8/2020 | EPI_ISL_411955 | Feb. 10, 2020 |
| B | derived | 258 BetaCovaapan/Hu_DP_Kng_19-020/2020 | EPI_ISL_412968 | Feb. 10, 2020 |
| B | derived | 259 BetaCov/Japan/Hu_DP_Kng_19-027/2020 | EPI_ISL_412969 | Feb. 10, 2020 |
| A | 29095T | 174 BetaCov/USA/TX1/2020 | EPI_ISL_411956 | Feb. 11, 2020 |
| B | derived | 262 BetaCov/Italy/CDG1/2020 | EPI_ISL_412973 | Feb. 20, 2020 |
| B | ancestral | 187 BetaCov/Hefei/2/2020 | EPI_ISL_412026 | Feb. 23, 2020 |
| B | derived | 227 BetaCov/USA/CA9/2020 | EPI_ISL_412862 | Feb. 23, 2020 |
| A | 29095C | 261 BetaCov/USA/WA2/2020 | EPI_ISL_412970 | Feb. 24, 2020 |
| B | derived | 253 BetaCov/Germany/Baden-Wuerttemberg-1/2020 | EPI_ISL_412912 | Feb. 25, 2020 |
| B | derived | 263 BetaCov/Mexico/CDMX/InDRE_01/2020 | EPI_ISL_412972 | Feb. 27, 2020 |
| B | derived | 265 BetaCov/Australia/NSW05/2020 | EPI_ISL_412975 | Feb. 28, 2020 |
| C | | 273 BetaCov/Brazil/SPBR-02/2020 | EPI_ISL_413016 | Feb. 28, 2020 |
| C | | 171 BetaCov/South Korea/SNU01/2020 | EPI_ISL_411929 | 2020 January |

Information obtained from Forster et al. "Phylogenetic network analysis of SARS-CoV-2 genomes," PNAS, 2020.

Additional exemplary SARS-CoV-2 strains are shown in Table 1B below.

| Name/Designation | Distribution | | Notable Mutation(s) | Impact | Sequence |
|---|---|---|---|---|---|
| D614G | | Worldwide | D614G | Increased infectivity, Dominant circulating since June 2020 | P0DTC2 |
| B.1.1.7 | 501Y.V1 | UK/Worldwide (nearly dominant in US) | D614G, N501Y, P681H | Increased infectivity | B.1.1.7 Lineages |
| B.1.351 | 501.V2, or N501Y.V2 | South Africa | N501Y, E484K*, K417N | Increased infectivity, **\*escape mutation\*** | B.1.351 Lineages |
| B.1.1.248 | P1 | Brazil | N501Y, E484K*, K417T | Increased infectivity, **\*escape mutation\*** | P1 Lineages |

In some cases, the coronavirus viral antigen is a coronavirus S protein peptide in a prefusion conformation, which is a structural conformation adopted by the ectodomain of the coronavirus S protein following processing into a mature coronavirus S protein in the secretory system, and prior to triggering of the fusogenic event that leads to transition of coronavirus S to the postfusion conformation. The three-dimensional structure of an exemplary coronavirus S protein (HKU1-CoV) in a prefusion conformation is provided in Kirchdoerfer et al., "Pre-fusion structure of a human coronavirus spike protein," Nature, 531: 118-121, 2016. In some cases, the coronavirus viral antigen is a coronavirus S protein peptide in a postfusion conformation.

In some cases, the coronavirus viral antigen comprises one or more amino acid substitutions, deletions, or insertions compared to a native coronavirus S sequence, such as one that provides for increased retention of the prefusion conformation compared to coronavirus S ectodomain trimers formed from a corresponding native coronavirus S sequence. In some cases, the coronavirus viral antigen is a fragment of an S protein peptide. In some embodiments, the antigen or immunogen is an epitope of an S protein peptide. Epitopes include antigenic determinant chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on coronavirus S ectodomain. Epitopes can be formed both from contiguous amino acids or noncontiguous amino acids juxtaposed by tertiary folding of a protein. In some embodiments, the coronavirus epitope is a linear epitope. In some embodiments, the coronavirus epitope is a conformational epitope. In some embodiments, the coronavirus epitope is a neutralizing epitope site. In some embodiments, one or more or all neutralizing epitopes of the coronavirus S protein peptide or fragment thereof are present as the antigen or immunogen, such as a receptor binding domain (RBD) peptide or fusion thereof, e.g., a receptor binding motif (RBM) peptide or fusion thereof.

In some embodiments, the viral antigen comprises a sequence of the spike glycoprotein of the original Wuhan-Hu-1 coronavirus (e.g., NC_045512). In some embodiments, the viral antigen comprises a sequence of the spike glycoprotein of a virus in the B.1.526 lineage. In some embodiments, the viral antigen comprises a sequence of the spike glycoprotein of a Cluster 5 (ΔFVI-spike) virus. In some embodiments, the viral antigen comprises a sequence of the spike glycoprotein of a virus in the B.1.1.7 lineage. In some embodiments, the viral antigen comprises a sequence of the spike glycoprotein of a virus in the B.1.1.207 lineage. In some embodiments, the viral antigen comprises a sequence of the spike glycoprotein of a virus in the B.1.1.317 lineage. In some embodiments, the viral antigen comprises a sequence of the spike glycoprotein of a virus in the B.1.1.318 lineage. In some embodiments, the viral antigen comprises a sequence of the spike glycoprotein of a virus in the P.1 lineage. In some embodiments, the viral antigen comprises a sequence of the spike glycoprotein of a virus in the B.1.351 lineage. In some embodiments, the viral antigen comprises a sequence of the spike glycoprotein of a virus in the B.1.429/CAL.20C lineage. In some embodiments, the viral antigen comprises a sequence of the spike glycoprotein of a virus in the B.1.525 lineage. In some embodiments, the viral antigen comprises a sequence of the spike glycoprotein of a virus in the B.1.526 lineage. In some embodiments, the viral antigen comprises a sequence of the spike glycoprotein of a virus in the B.1.617 lineage. In some embodiments, the viral antigen comprises a sequence of the spike glycoprotein of a virus in the B.1.617.2 lineage (e.g., the Delta variant). In some embodiments, the viral antigen comprises a sequence of the spike glycoprotein of a virus in the B.1.618 lineage. In some embodiments, the viral antigen comprises a sequence of the spike glycoprotein of a virus in the B.1.620 lineage. In some embodiments, the viral antigen comprises a sequence of the spike glycoprotein of a virus in the P.2 lineage. In some embodiments, the viral antigen comprises a sequence of the spike glycoprotein of a virus in the P.3 lineage. In some embodiments, the viral antigen comprises a sequence of the spike glycoprotein of a virus in the B.1.1.143 lineage. In some embodiments, the viral antigen comprises a sequence of the spike glycoprotein of a virus in the A.23.1 lineage. In some embodiments, the viral antigen comprises a sequence of the spike glycoprotein of a virus in the B.1.617 lineage. In some embodiments, the viral antigen comprises sequences derived from the spike glycoproteins of any two or more viruses, in any suitable combination, selected from the group consisting of Wuhan-Hu-1, a virus in the B.1.526 lineage, a virus in the B.1.1.7 lineage, a virus in the P.1 lineage, a virus in the B.1.351 lineage, a virus in the P.2 lineage, a virus in the B.1.1.143 lineage, a virus in the A.23.1 lineage, and a virus in the B.1.617 lineage.

In some embodiments, the viral antigen comprises E484K and/or S477N, e.g., as in a B.1.526 variant. In some embodiments, the viral antigen comprises 4400-402 (ΔFVI), e.g., as in a Cluster 5 (ΔFVI-spike) variant. In some embodiments, the viral antigen comprises 469-70 (ΔHV), Δ144 (ΔY), N501Y, A570D, D614G, P681H, T716I, S982A, and/or D1118H, e.g., as in a B.1.1.7 variant. In some embodiments, the viral antigen comprises P681H, e.g., as in a B.1.1.207 variant. In some embodiments, the viral antigen comprises L18F, T20N, P26S, D138Y, R190S, K417T, E484K, N501Y, D614G, H655Y, T1027I, and/or V1176F, e.g., as in a P.1 variant. In some embodiments, the viral antigen comprises E484K, e.g., as in a P.2 variant. In some embodiments, the viral antigen comprises E484K and/or N501Y, e.g., as in a P.3 variant. In some embodiments, the viral antigen comprises L18F, D80A, D215G, Δ242-244 (ΔLAL), R246I, K417N, E484K, N501Y, D614G, and/or A701V, e.g., as in a B.1.351 variant. In some embodiments, the viral antigen comprises S13I, W152C, and/or L452R, e.g., as in a B.1.429/CAL.20C variant. In some embodiments, the viral antigen comprises Δ69-70 (ΔHV), E484K, and/or F888L, e.g., as in a B.1.525 variant. In some embodiments, the viral antigen comprises G142D, L452R, E484Q, and/or P681R, e.g., as in a B.1.617 variant. In some embodiments, the viral antigen comprises G142D, L452R, and/or P681R, e.g., as in a B.1.617.2 variant. In some embodiments, the viral antigen comprises E484K, e.g., as in a B.1.618 variant. In some embodiments, the viral antigen may comprise a polypeptide comprising any one or more of the aforementioned mutations in any suitable combination.

In nature, the spike protein (also referred to as spike glycoprotein, or S protein) of coronaviruses mediate viral entry into the host cells. Table 2 below shows identified viral receptors for various coronaviruses. See, also, Raj V S et al. Chapter 15 of Helena Jane Maier et al. (eds.), Coronaviruses: Methods and Protocols, Methods in Molecular Biology, vol. 1282, Springer Science+Business Media New York 2015; Li F. Annu Rev Virol. 2016; 3(1): 237-261; Hulswit 2019 and Zhou et al., Nature 579: 270, 2020, which are incorporated herein by reference in their entirety.

TABLE 2

Host viral receptors for coronaviruses.

| Viral receptor on host cells | Coronavirus |
|---|---|
| aminopeptidase N (APN) | HCoV-229E, TGEV, PEDV, PRCV, FIPV, CCoV |
| angiotensin-converting enzyme 2 (ACE2) | SARS-CoV2, SARS-CoV, HCoV-NL63 |
| dipeptidyl peptidase 4 (DPP4, also known as CD26) | MERS-CoV, HKU4 |
| N-acetyl-9-O-acetylneuraminic acid (9-O-Ac-Neu5Ac) | HCoV-OC43, HCoV-HKU1, BCoV |
| murine carcinoembryonic antigen related adhesion molecule 1 (mCEACAM) | MHV |

A naturally-occurring spike protein of a coronavirus forms homotrimers protruding from the viral surface. The S protein comprises two functional subunits responsible for binding to the host cell receptor (S1 subunit) and fusion of the viral and cellular membranes (S2 subunit). For many CoVs, S is cleaved at the boundary between the S1 and S2 subunits, which remain non-covalently bound in the prefusion conformation. The distal S1 subunit comprises the receptor-binding domain(s) and contributes to stabilization of the prefusion state of the membrane-anchored S2 subunit that contains the fusion machinery. For CoVs, S is further cleaved by host proteases at the so-called S$_2$' site located immediately upstream of the fusion peptide. This cleavage has been proposed to activate the protein for membrane fusion via extensive irreversible conformational changes. As a result, coronavirus entry into susceptible cells is a complex process that requires the concerted action of receptor-binding and proteolytic processing of the S protein to pro-mote virus-cell fusion. See, Walls et al., Cell 180, 281-292, 2020.

The spike protein of SARS-CoV-2 can be cleaved by both furin at the S1/S2 site and the transmembrane protease/serine (TMPRSS) protease 2, TMPRSS2, at the S2' site. See, Hoffman et al., Cell 181, 271-280, 2020. The furin cleavage site of SARS-CoV-2 locates between amino acids 685 and 686 of the S protein. SARS-CoV-2 and SARS-CoV both use ACE2 as the receptor to enter human cells. See, Zhou et al., Nature 579: 270, 2020.

In any of the embodiments herein, a viral receptor can be an intact receptor or a functional domain, subunit, or fragment thereof, or a fusion polypeptide (e.g., at least a portion of a Fc region, such as a functional Fc fragment, fused to at least a portion of a protein receptor), such as an Fc-ACE2 fusion polypeptide.

In any of the embodiments herein, a viral antigen can be an intact protein or a functional domain, subunit, or fragment thereof, or a fusion polypeptide (e.g., at least a portion of a Fc region, such as a functional Fc fragment, fused to at least a portion of a viral antigen), such as an Fc-S protein fusion polypeptide, e.g., an Fc-RBD fusion polypeptide.

In any of the embodiments where the antigen (e.g., S protein) is on a solid phase (e.g., particles), the sample and a labeled receptor (e.g., ACE2) can be mixed with the particles at the same time. In any of the embodiments where the antigen (e.g., S protein) is on a solid phase (e.g., particles), the sample and a labeled receptor (e.g., ACE2) can be mixed with the particles a few seconds apart, e.g., 2, 3, 4, 5, 6, 7, 8, 9, 10, or between about 10 and about 15, or between about 15 and about 20 seconds apart. In some embodiments, the sample is mixed with the particles first, before a labeled receptor (e.g., a solution containing labelled ACE2) is added to the reaction mix. In some embodiments, the sample is mixed with labeled receptor (e.g., a solution containing labelled ACE2) first, before the particles are added to the reaction mix. This way, in some aspects, unfavorable binding competition between the antigen (e.g., S protein) with the neutralizing antibody in the sample and with the receptor (e.g., ACE2) can be avoided or reduced.

As used herein, "spike protein" or "S protein" refers to a naturally-occurring spike protein or an engineered derivative having one or more mutations (e.g., insertion, deletion, substitution, etc.) to the amino acid sequence of a naturally-occurring spike protein. When present in a virus, a naturally-occurring spike protein protrudes from the viral capsid or viral envelope, and binds to certain receptors on a host cell to mediate viral entry into the host cell. An engineered derivative of a naturally-occurring spike protein retains serological reactivity as the naturally-occurring spike protein, but may or may not retain binding activity to the viral receptor(s) on the host cell. In some embodiments, an engineered spike protein has at least about 80% (e.g., at least about any one of 81%, 82%, 83%, 84%, 85%, 86%, 87%, 88%, 89%, 90%, 91%, 92%, 93%, 94%, 95%, 96%, 97%, 98%, or more) sequence identity to a naturally-occurring spike protein. In some embodiments, an engineered spike protein shares the same epitope as a naturally-occurring spike protein with respect to an antibody present in a host.

As used herein, the term "antibody" or "antibody moiety" includes full-length antibodies (including full-length 4-chain antibodies or full-length heavy chain antibodies, which have an immunoglobulin Fc region), antigen-binding fragments thereof, and B-cell receptors (BCRs).

As used herein, a "neutralizing antibody" refers to an antibody that defends a host cell from an infectious agent by neutralizing any effect (e.g., cytotoxicity) it has biologically. A "non-neutralizing antibody" refers to an antibody that specifically binds to an infectious agent, but is incapable of ameliorating the biological effects of the infectious agent on the host cell. A "sub-neutralizing antibody" refers to an antibody that is capable of partially neutralizing the biological effects of the infectious agent on the host cell. A subneutralizing antibody may ameliorate one or more biological effects of an infectious agent on the host cell by no more than about any one of 90%, 80%, 70%, 60%, 50%, 40%, 30%, 20%, 10% or less compared to a neutralizing antibody.

A full-length four-chain antibody comprises two heavy chains and two light chains. The variable regions of the light and heavy chains are responsible for antigen-binding. The variables region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of $\alpha$, $\delta$, $\epsilon$, $\gamma$, and $\mu$ heavy chains, respectively. Several of the major antibody classes are divided into subclasses such as IgG1 ($\gamma$1 heavy chain), IgG2 ($\gamma$2 heavy chain), IgG3 ($\gamma$3 heavy chain), IgG4 ($\gamma$4 heavy chain), IgA1 ($\alpha$1 heavy chain), or IgA2 ($\alpha$2 heavy chain).

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs. The variable region of a heavy chain-only antibody is referred herein as "VHH." A VHH is one type of single-domain antibody. A "single-domain antibody" or "sdAb" refers to a single antigen-binding polypeptide having three complementary determining regions (CDRs). The sdAb alone is capable of binding to the antigen without pairing with a corresponding CDR-containing polypeptide. Some $V_H$Hs may also be known as Nanobodies. Camelid $V_H$H is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

The term "B-cell receptor" or "BCR" refers to a membrane-bound immunoglobulin molecule ("mIg"), which is associated with an Ig$\alpha$/Ig$\beta$ (CD79a/CD79b) heterodimer ($\alpha$/$\beta$). An mIg subunit binds to an antigen to induce aggregation of the receptors, while an $\alpha$/$\beta$ subunit transmits a signal to the inside of a B cell. BCRs, when aggregated, are understood to quickly activate Lyn, Blk, and Fyn of Src family kinases as in Syk and Btk of tyrosine kinases. Results greatly differ depending on the complexity of BCR signaling, the results including survival, resistance (allergy; lack of hypersensitivity reaction to antigen) or apoptosis, cell division, differentiation into antibody-producing cell or memory B cell and the like. B cells producing antibodies also express B-cell receptors on cell surface, which have the same immunoglobulin binding sequences as those of the antibodies the B cells produce.

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a $V_H$H, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

As use herein, the term "specifically binds" or "is specific for" refers to measurable and reproducible interactions, such as binding between a target and an antibody or antibody moiety that is determinative of the presence of the target in the presence of a heterogeneous population of molecules, including biological molecules. For example, an antibody moiety that specifically binds to a target (which can be an epitope) is an antibody moiety that binds the target with greater affinity, avidity, more readily, and/or with greater duration than its bindings to other targets. In some embodiments, an antibody moiety that specifically binds to an antigen reacts with one or more antigenic determinants of the antigen with a binding affinity that is at least about 10 times its binding affinity for other targets.

The terms "target-binding moiety" and "antigen-binding moiety" are used herein interchangeably. In some embodiments, an antigen-binding moiety is an antibody fragment. In some embodiments, an antigen-binding moiety is not derived from an antibody.

As used herein, a "homogeneous assay" refers to an assay format allowing to make an assay-measurement by a simple mix and read procedure without the necessity to process samples by separation or washing steps. Some assays can be carried out simply by mixing the reagents and sample and making a physical measurement. Such assays are called homogeneous assays, or less frequently non-separation assays. In a competitive, homogeneous assay, unlabeled analyte (e.g., neutralizing antibodies) in a sample competes with a labelled reagent (e.g., a labelled viral antigen or a labelled viral receptor) for binding to another reagent (e.g., the viral receptor or the viral antigen). The amount of labelled, unbound analyte is then measured. In theory, the more analyte in the sample, the more labelled reagent gets displaced and then measured.

As used herein and in the appended claims, the singular forms "a," "an," and "the" include plural referents unless the context clearly dictates otherwise.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

In some aspects, provided herein are kits for analyzing a sample, wherein the kit comprises: a) beads; b) a first assay reagent (a capture reagent) comprising a surface antigen from a coronavirus; and c) a second assay reagent (a detection reagent) comprising a receptor for the surface antigen conjugated to a detectable label such as one or more chemiluminescent signal generating molecules. The bead such as magnetic microbeads can be coated with the surface antigen to form the first assay reagent. In some embodiments, the surface antigen of the coronavirus can be the S protein of SARS-CoV-2, or a fragment, antigenic sequence, or epitope thereof. In some embodiments, the receptor is human Angiotensin-Converting Enzyme 2 (hACE2). In some embodiments, the chemiluminescent signal generating molecules can comprise Acridinium Ester (AE), N-(4-aminobutyl)-N-ethylisoluminol (ABEI), Alkaline Phosphatase (AP), and/or Horseradish Peroxidase (HRP).

In some embodiments, the kits described herein can be used in a method for analyzing a sample, comprising: contacting the sample with a particle coated with a surface antigen from a coronavirus, and with a receptor for the surface antigen which is labelled with a detectable moiety, wherein the sample comprises or is suspected of comprising an antibody that reduces or inhibits binding between the surface antigen and the receptor, wherein labelled receptors that specifically bind to the surface antigen are immobilized on the particle via the surface antigen, wherein the antibody, if present in the sample, competes with or displaces one or more of the labelled receptors, and wherein a signal is detected on the particle, and a magnitude of the signal is inversely proportional to an amount or level of the antibody in the sample.

The present kits can comprise any additional suitable reagents or components. In some embodiments, the present kits comprise means for assessing inhibition of binding between the SARS-CoV-2 Spike ("S") protein Receptor Binding Domain (RBD) and the receptor to determine the presence of SARS-CoV-2 neutralizing antibodies in a sample.

IgM and IgG antiviral antibodies can be detected in the serum samples of infected patients. After infection with SARS-CoV-2, virus antigens stimulate the immune system to produce antibodies that can be detected in the blood. Among these antibodies, SARS-CoV-2 IgM antibodies appears early and are mostly positive 3-5 days after onset of symptoms. The SARS-CoV-2 IgM titers then decrease while the SARS-CoV-2 IgG antibody potency starts to rise rapidly. During the recovery phase, the titer of the SARS-CoV-2 IgG antibody may increase four times or more compared to the acute phase.

In some aspects, neutralizing antibodies include a subset of antibodies that bind to the virus in a manner that blocks infection. A neutralizing antibody might block interactions with a cellular receptor, or bind to a viral capsid in a manner that inhibits the uncoating of the viral genome. Only a small subset of the many antibodies that bind a virus are capable of neutralization. A recent longitudinal study showed that neutralizing antibody responses to SARS-CoV-2 can be detected in most infected individuals 10-15 d after the onset of COVID-19 symptoms. A peak response was detected 3-4 weeks post-infection, which then wanes.

Current commercial SARS-CoV-2 total IgG antibody assays do not differentiate between neutralizing antibodies and non-neutralizing antibodies, and give poor NPA for SARS-CoV-2 neutralization. A robust serological assay that specifically detects neutralizing antibodies to SARS-CoV-2 is urgently needed to assess not only infection rates, herd immunity and predicted humoral protection, but also vaccine efficacy during clinical trials and after large-scale vaccination campaigns. In some embodiments, an automated SARS-CoV-2 neutralizing antibody assay disclosed herein uses viral antigen protein S-RBD and human ACE2 receptor to assess the presence of neutralizing antibodies in a patient sample. The assay can run on a fully automated immunoassay chemiluminescent analyzer. Because its ability to mimic the in vivo virus-host interaction and vector-based neutralization assays (pVNT), the assay is a faster and safer alternative to the traditional, low throughput, live virus cell-based assays for neutralizing antibodies.

In some embodiments, an automated assay disclosed herein is a competitive chemiluminescence immunoassay. Sample, magnetic microbeads, capture reagent (containing SARS-CoV-2 viral antigen S-RBD) and a detection reagent (e.g., containing the human ACE2 receptor conjugated to ABEI) can be mixed thoroughly and incubated, forming specific immune-complexes. After precipitation in a magnetic field and supernatant decanting, the magnetic particles are subjected to wash cycles. Subsequently, one or more solutions can be added to initiate a chemiluminescent reaction. In the presence of neutralizing antibodies in the sample, these antibodies bind to the viral antigen protein coated on the magnetic particles and block the interaction between the viral protein and the human ACE2 receptor, resulting a decrease in the chemiluminescent signal (RLU). The amount of the neutralizing antibody in a sample is inversely proportional to the RLU signal.

In some embodiments, disclosed herein a kit comprising one or more of the following components, in any suitable combination: magnetic beads (e.g., in PBS buffer containing BSA, sodium azide (e.g., <0.1%)); a capture reagent containing a human SARS-CoV-2 antigen protein S-RBD in PBS buffer supplemented with BSA and sodium azide (e.g., <0.1%); a detection reagent containing a human ACE2 receptor in PBS buffer supplemented with BSA and sodium azide (e.g., <0.1%); a Calibrator Low: SARS-CoV-2 neutralizing antibody in pooled serum with preservatives (sodium azide e.g., <0.1%); a Calibrator High: SARS-CoV-2 neutralizing antibody in pooled serum with preservatives (sodium azide e.g., <0.1%); a Control Low: SARS-CoV-2 neutralizing antibody in pooled serum with preservatives (sodium azide e.g., <0.1%); and a Control High: SARS-CoV-2 neutralizing antibody in pooled serum with preservatives (sodium azide e.g., <0.1%). All components of the kit can be provided ready-to-use. In some embodiments, two or more components of the kit are packaged together. In some embodiments, a component of the kit is packaged separately.

The present methods and kits can be used with any suitable reaction time. In some embodiments, the present methods have a total assay time that is at about 60 minutes or shorter, e.g., about 59, 58, 57, 56, 55, 54, 53, 52, 51, 50, 49, 48, 47, 46. 45, 44, 43, 42, 41, 40, 39, 38, 37, 36, 35, 34, 33, 3, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 minutes or 1 minute. For example, the present methods can have an assay time from initiation, e.g., addition of a sample and/or a reagent(s), to signal readout time, that is at about 60 minutes or shorter, e.g., about 59, 58, 57, 56, 55, 54, 53, 52, 51, 50, 49, 48, 47, 46. 45, 44, 43, 42, 41, 40, 39, 38, 37, 36, 35, 34, 33, 3, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 minutes or 1 minute.

The present methods and kits can be used with any suitable analytic instruments. In some embodiments, the present methods are conducted on a general chemistry analyzer or a clinical chemistry analyzer, e.g., general chemistry analyzer or clinical chemistry analyzer from Roche, Hitachi, Modular P, Cobas series, Beckman/Olympus AU series, Beckman Synchron and DXC series, or Abbot Architect series.

The present methods and kits can be used to achieve any suitable precision. In some embodiments, the present methods can be conducted to achieve a precision or CV of about 30% or less, e.g., about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less. For example, the present methods can be conducted to achieve a precision or CV of about 5% or less, e.g., about 5%, 4%, 3%, 2.5%, 2%, 1.5% 1%, 0.5% or less for an antibody level (e.g., a neutralizing antibody level) of about 30 ng/ml or less, e.g., about 30 ng/ml, 25 ng/ml, 20 ng/ml, 15 ng/ml, 10 ng/ml, 5 ng/ml, 4 ng/ml, 3 ng/ml, 2 ng/ml, 1 ng/ml, or less. In another example, the present methods can be conducted to achieve a precision or CV of about 10% or less, e.g., about 10%, 9%, 8%, 7%, 6%, 5%, 4.5%, 4.0%, 3%, 2.5%, 2%, 1.5% 1%, 0.5% or less for an antibody level (e.g., a neutralizing antibody level) of about 100 ng/ml or less, e.g., about 100 ng/ml, 90 ng/ml, 80 ng/ml, 70 ng/ml, 60 ng/ml, 50 ng/ml, 40 ng/ml, 30 ng/ml, 20 ng/ml, 10 ng/ml, or less.

EXAMPLES

The following examples are included for illustrative purposes only and are not intended to limit the scope of the present disclosure.

Example 1: Chemiluminescence Immunoassay for SARS-CoV-2 Neutralizing Antibodies Magnetic particles are coated with the SARS-CoV-2 Spike ("S") protein Receptor Binding Domain (RBD) either directly via stable covalent bonding (such as an amide bond) or through a streptavidin (or a neutravidin) biotin interaction, whereby streptavidin (or neutravidin) is first covalently bonded to the magnetic particle then mixed with biotinylated RBD.

hACE2 is labeled with a chemiluminescence-generating molecule such as Acridinium Ester (AE), N-(4-aminobutyl)-N-ethylisoluminol (ABEI), or Alkaline Phosphatase (AP).

Serum or plasma samples containing or suspected of containing SARS-CoV-2 neutralizing antibodies are first mixed with the RBD-conjugated magnetic particles, and then, after a few wash cycles, with the labeled hACE2, which serves as a tracer or competitor.

After incubation, the magnetic particles are washed, and chemiluminescence signaling substrate(s) is (are) added to generate a chemiluminescence signal measured in RLU. The measured chemiluminescence signal is inversely proportional to the amount of SARS-CoV-2 neutralizing antibodies present in the sample.

Reagent Composition:

| Reagent | Composition |
| --- | --- |
| R1 (capture reagent) | 0.01-1.0% Magnetic microbeads coated with SARS-CoV-2 RBD in 1X PBS buffer + 5-25% Sucrose + 0.01-1% Tween 20 + 0.05-5% BSA + 0.09% Sodium Azide |
| R2 (detection reagent) | 0.001-5.0 □ g/mL hACE2 labeled with ABEI in 1X PBS buffer + 0.01-1% Tween 20 + 0.05-5% BSA + 0.09% Sodium Azide |

An exemplary assay scheme is shown in FIG. 1, which can be performed on the DZ-Lite 300 Plus series of analyzers.

Example 2: Latex-Enhanced Immunoassay for SARS-CoV-2 Neutralizing Antibodies A first type of polystyrene particles (latex particles A) are coated with the hACE2 protein either directly via stable covalent bonding (such as an amide bond) or through a streptavidin (or a neutravidin) biotin interaction. A second type of polystyrene particles (latex particles B) are coated with the SARS-CoV-2 Spike protein RBD. In the absence of SARS-CoV-2 neutralizing antibodies, latex particles A and latex particles B agglutinate readily and generate a signal that can be measured spectrophotometrically.

When serum or plasma samples containing SARS-CoV-2 neutralizing antibodies are mixed with the latex particles A and particles B, an inhibition of the agglutination reaction between the particles A and particles B is initiated. The extent of agglutination can be measured spectrophotometrically and is inversely proportional to the amount of SARS-CoV-2 neutralizing antibodies present in the serum or plasma sample.

Reagent Composition:

| Reagent | Composition |
| --- | --- |
| Diluent | 0.05-0.5M Tris-HCl pH 6.0-8.0 + 8-20% Choline Chloride + 0.1-5% Sodium Chloride + 0.01-1.0% Tween 20 + 0.1-2.0% Polyethylene glycol + 0.09% Sodium azide. |
| R1 | 0.05-0.5 M Tris-HCl pH 6.0-8.0 + 0.1-5% Sodium Chloride + 0.01-1.0% Tween 20 + 0.01-1.0% latex particles A (coated with hACE2) + 0.09% Sodium azide. |
| R2 | 0.05-0.5M Tris-HCl pH 6.0-8.0 + 0.1-5% Sodium Chloride + 0.01-1.0% Tween 20 + 0.01-1.0% latex particles B (coated with SARS-CoV-2 RBD) + 0.09% Sodium azide. |

Figure 2:
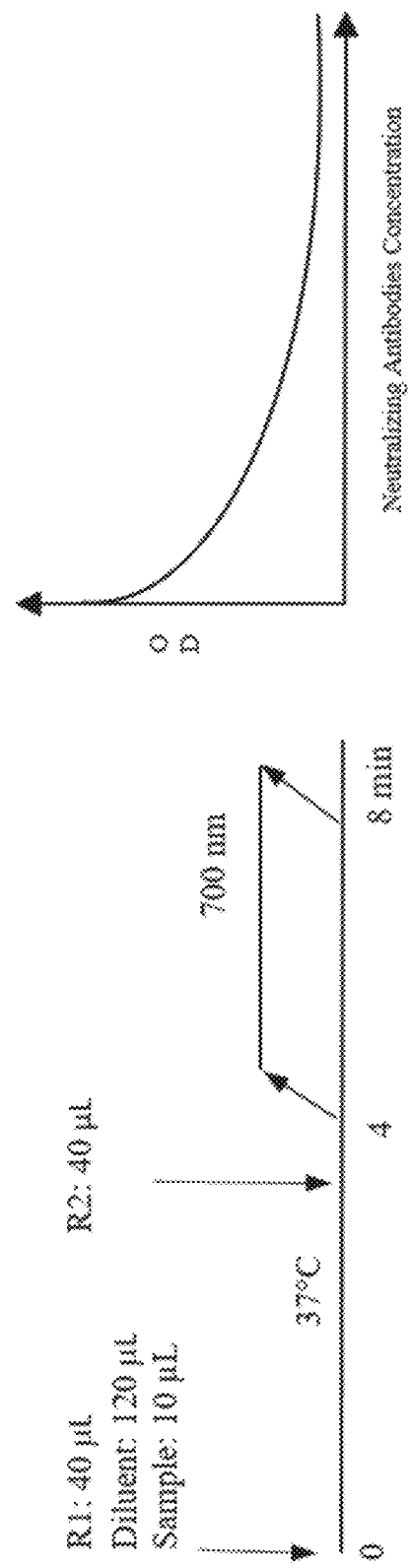
FIG. 2 shows an exemplary assay scheme utilizing a homogeneous assay format with coated latex particles.

An exemplary assay scheme is shown in FIG. 2, which can be performed on Beckman Coulter AU680, AU400 and similar series of chemistry analyzers.

Example 3: Validation and Performance of an Automated SARS-CoV-2 Neutralizing Antibody Detection Assay Experiments were performed to assess the utility and performance of an automated chemiluminescent immunoassay for semi-quantitative detection of antibodies that neutralize SARS-CoV-2. The automated immunoassay was performed using a DZ-Lite 3000 Plus Chemiluminescence Analyzer. Manual steps were limited to using a computer interface to input commands and loading sample racks and reagent cartridges. In contrast to other rapid tests and point of care devices, operator decision-making is not involved in the outcome of any results. Rather, the analyzer automatically provides results in AU/mL. Immunoassay precision, cross-reactivity, and clinical agreement with a comparator, among other aspects, were evaluated in the experiments that follow.

Precision

Precision, commensurate with reproducibility, is defined in terms of coefficient of variation (% CV) or standard deviation (SD). Precision testing was performed on a DZ-Lite 3000 Plus instrument in accordance with the CLSI EP5-A3 protocol. An acceptable CV was set at ≤20%. Precision was evaluated on one negative control, two positive controls (one low and one high, namely control 1 and control 2) and four serum samples (one negative and three positives, namely S0, S1, S2 and S3). To evaluate day-to-day precision, testing was performed over the course of three days, on two different instruments, at the rate of two runs per day. Separate lots of reagents were prepared for testing (Lot 1 and Lot 2), and two replicates were included per run. All measurements were in AU/mL (arbitrary unit per mL).

Precision was evaluated within-run, between-run, day-to-day, and between-lot. One advantage of evaluating day-to-day precision is that the results can provide insight into the reproducibility of realistic routine operating conditions. Statistical analyses of the precision data for Lot 1 and Lot 2, separately and in combination, were performed using EP Evaluator Software.

The results of the precision studies demonstrated that the within-run, between-run, day-to-day, between-lot and total % CV or SD (for all tested samples and controls, including negative specimens) met the acceptance criteria of ≤20% CV (data not shown). When analyzing the Lots in combination, the four lowest % CVs were determined for the positive controls (control 1 and control 2) and two positive serum samples (S2 and S3), indicating high reproducibility for detection of neutralizing antibodies in a positive SARS-CoV-2 serum sample.

Detection Limits

The Limit of Blank (LOB), Limit of Detection (LOD), and Limit of Quantitation (LOQ) of the automated immunoassay were determined according to the CLSI EP17-A2 Approved Guidelines.

LOB

LOB is the highest value likely (with 95% confidence) to be observed for a negative sample. In this study, 30 replicates of blank samples per reagent lot were analyzed. The 95th percentile of 30 blank replicates is the LOB estimate for each lot. The LOB of the assay is the maximum of two reagent lots LOBs. LOB can be interpreted as the value below which is the result is interpreted as "not detected."

The LOB was estimated by measuring five known negative samples (N1 to N5) over three days at the rate of two replicates per day and using two lots of reagents. This protocol resulted in 30 replicates of blank samples per lot. The 95th percentile of these 30 blank replicates was the LOB estimate for each lot. The claimed LOB for the assay was the highest LOB of the two lots tested. The LOB for Lot 1 was 0.0649 AU/mL, and the LOB for Lot 2 was 0.0792 AU/mL. Therefore, the assay LOB, the highest of the two lots, was 0.0792 AU/mL.

LOD

LOD is the minimum concentration that has results "detected" 95% of the time. In this study, 30 replicates of low-level samples per reagent lot were tested. Estimates of LOD for each reagent lot were performed per CLSI EP17 guidelines. The LOD of the assay is the greatest LOD of the two reagent lots.

To determine the LOD, five samples (L1 to L5) containing low levels of analyte (positive patient samples diluted by known negative patient samples) were analyzed. Each sample was tested in duplicate over three days, using two lots of reagents. The LOD was calculated using the following equation:

$$LOD = LOB + (1.645 * \text{Standard Deviation of Low Samples})$$

From the raw data, the calculated LOD for Lot 1 was 0.332 AU/mL, and the calculated LOD for Lot 2 was 0.326 AU/mL. Thus, the assay LOD was 0.332 AU/mL.

LOQ

The Limit of Quantitation is defined as the lowest amount of analyte in a sample that can be accurately quantified with a CV≤20%. The LOQ was determined using five serum samples (Q1 to Q5) containing different known levels of analyte targeted at the estimated LOQ (positive patient samples diluted by negative patient samples). Each sample was tested in duplicate over three days, using two lots of reagents. The LOQ was estimated using the 95% confidence interval (CI) of the % CV vs concentration plot (as processed by the EP Evaluator Software, version 12.0). The LOQ of Lot 1 was 0.518 AU/mL, and the LOQ of Lot 2 was 0.558 AU/mL. Therefore, the assay LOQ was 0.558 AU/mL.

Linearity

Linearity studies define a range wherein the results of a method are directly proportional to the inputs, reflecting a linear, not curved, relationship. At a minimum, five dilutions should be within the linear range. Accepted Linear regression of the plot (Estimated Value vs Mean Recovery) was set at a slope of 0.9+/−0.1 and an $R^2$-value of $R^2 > 0.95$. Deviation from linearity for each dilution is the difference between the mean values of replicates and the best fitted straight line. Acceptable deviations from linearity were ≤15%.

The study was performed according to CLSI EP6-A—Evaluation of the Linearity of Quantitative Measurement Procedures: A Statistical Approach; Approved Guideline (April 2003). Linearity of the neutralizing antibody assay was evaluated by diluting SARS-CoV-2 positive serum samples with a negative pooled serum (100%, 75%, 50%, 25% and 0%). The undiluted positive serum sample had a read out of 29.3 AU/mL. Five samples ranging in expected AU/ml from 0-29.3 AU/mL were tested in triplicate. After plotting Expected Value versus Mean Recovery, linear regression of the graph was used to compute the Estimated Value for each linearity level. Deviation from linearity was calculated according to the following formula:

$$\text{Deviations from linearity (\%)} = [(\text{Mean Recovery} - \text{Estimated Value})/\text{Estimated Value}] \times 100.$$

Figure 3:
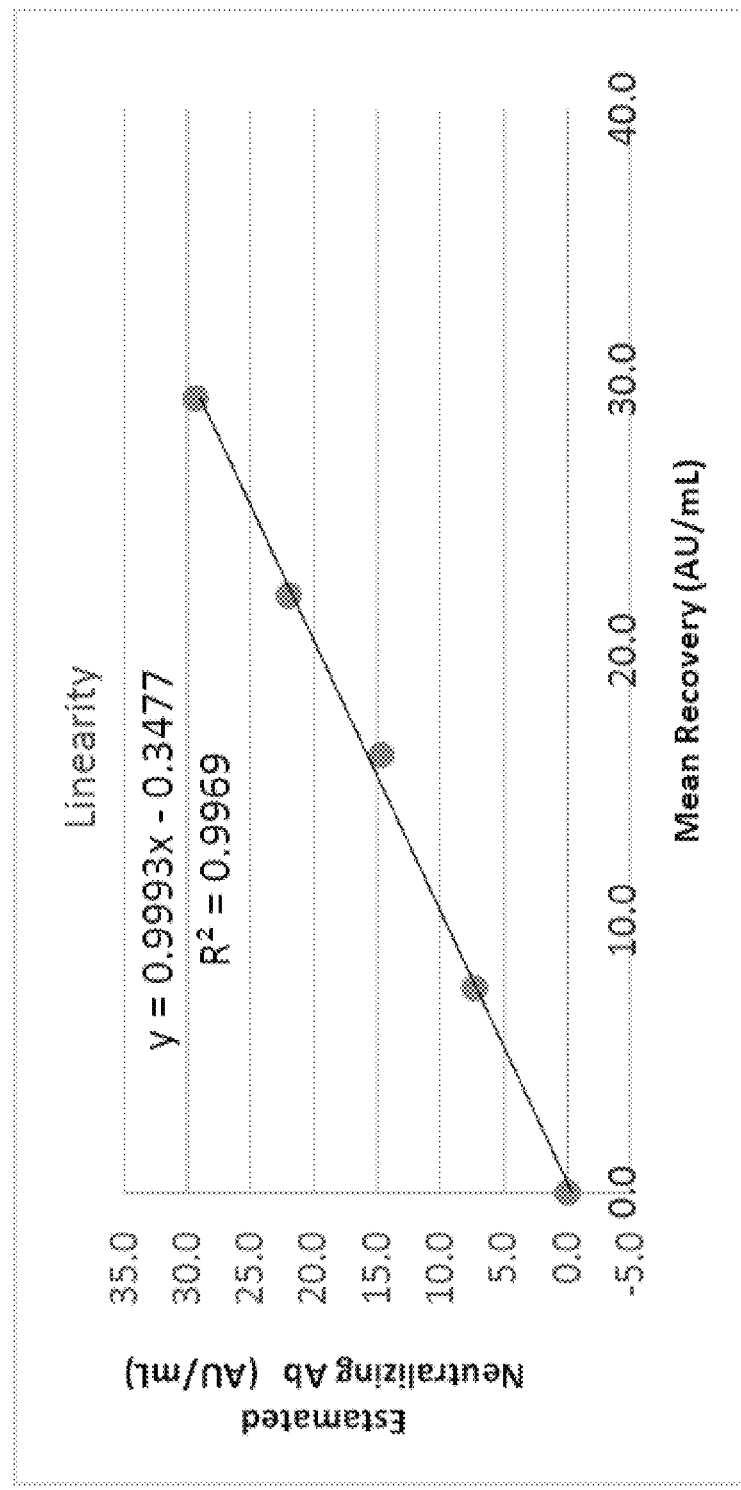
FIG. 3 shows a plot of estimated value of neutralizing antibodies (AU/mL) versus mean recovery (AU/mL) and the resultant slope and $R^2$-value used to determine deviation from linearity.

FIG. 3 shows a plot of Estimated Value versus Mean Recovery and the resultant slope and $R^2$-value. Deviation (%) did not exceed 15% at any point during the study (data not shown). Both the slope (0.9993) and $R^2$-value (0.9969) exceeded the set criteria (0.9+/−0.1 and 0.95, respectively), indicating exceptional linearity.

Matrix Comparison

A matrix comparison was performed to determine the effect of different matrices, e.g., serum and plasma, on method results. Twenty individual matched samples of serum, EDTA plasma, and lithium heparin plasma were used in this study. To cover the dynamic range of the assay, samples were spiked with SARS-CoV-2 purified neutralizing antibodies from a commercial source. To prevent alteration of the specimen matrix, volumes and dilutions were minimal. Measurements were performed in duplicate, and linear regression analysis was performed using the raw data. Acceptance criteria were defined as linear regression of a serum vs plasma slope within the range of 0.95-1.05 and an $R^2 \geq 0.95$.

Figure 4:
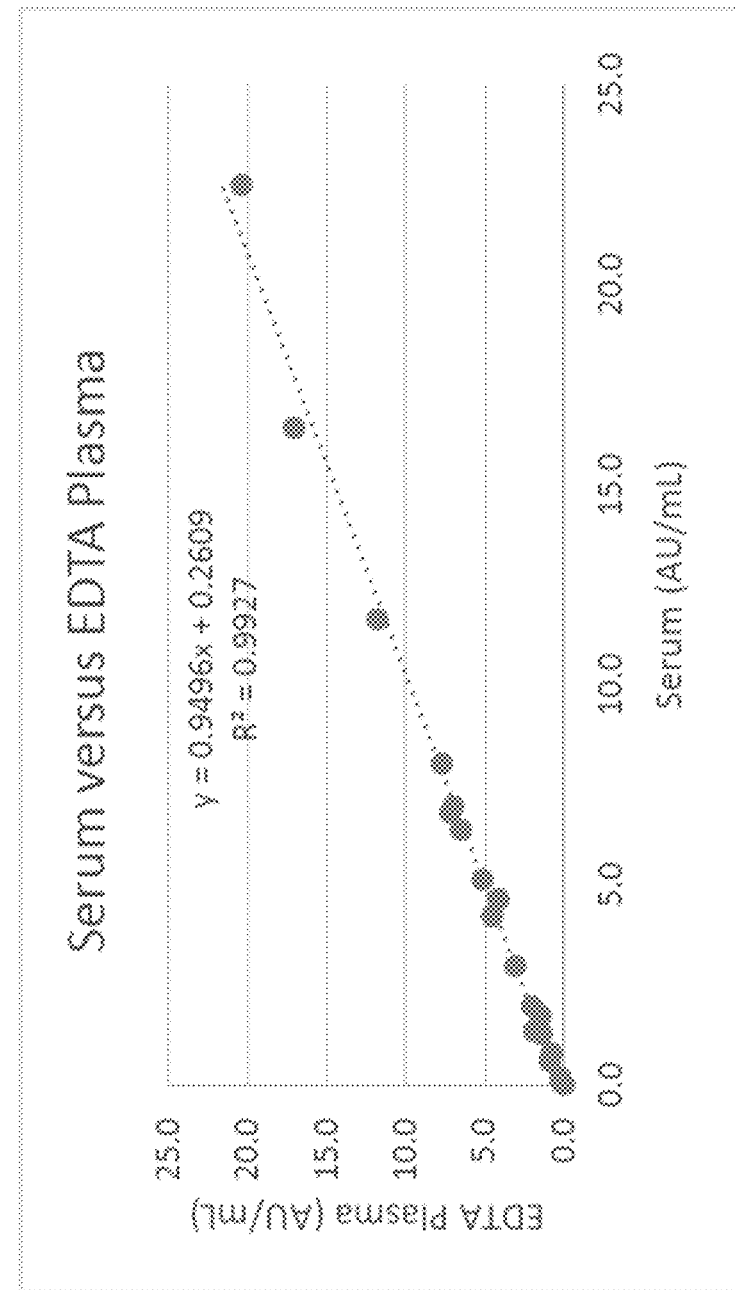
FIG. 4 shows a linear regression of serum (AU/mL) and EDTA plasma (AU/mL) spiked with SARS-CoV-2 purified neutralizing antibodies (n=3).
Figure 5:
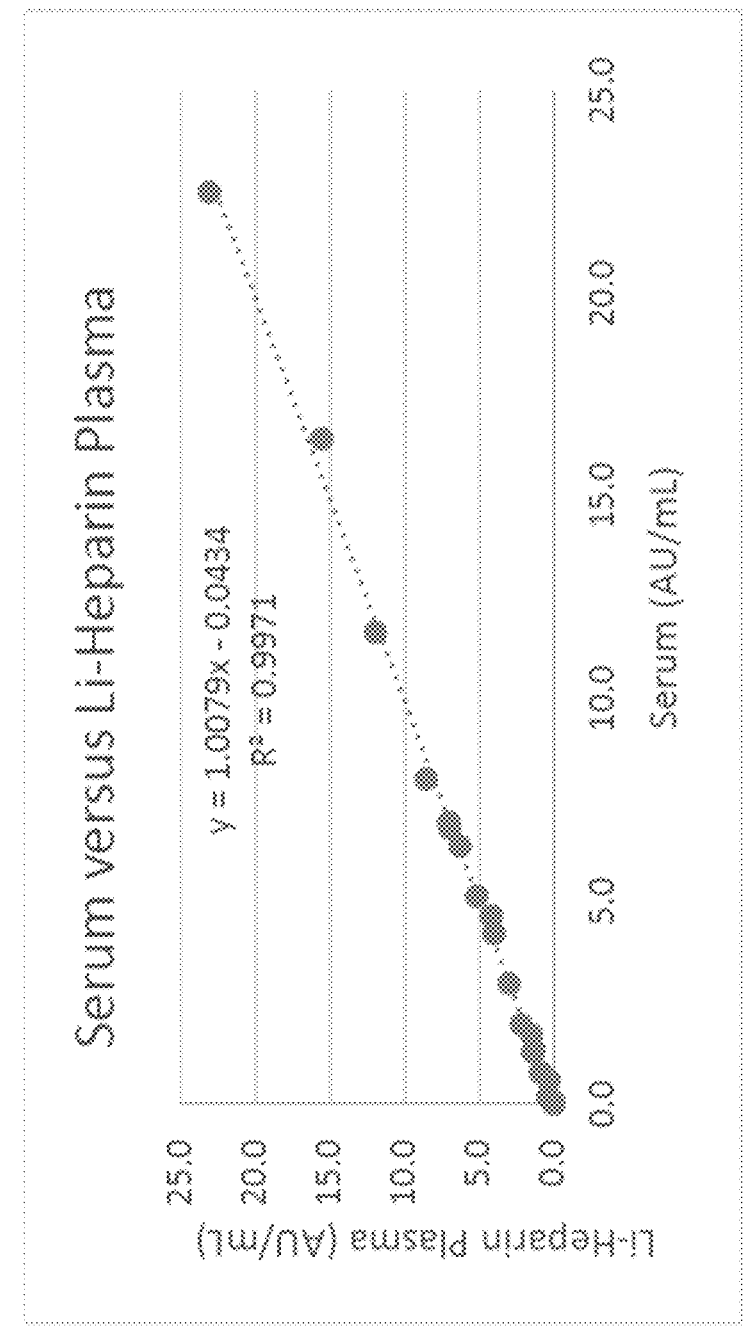
FIG. 5 shows a linear regression of serum (AU/mL) and Li-heparin plasma (AU/mL) spiked with SARS-CoV-2 purified neutralizing antibodies (n=3).

FIG. 4 shows a plot of serum versus EDTA plasma. FIG. 5 shows a plot of serum versus Li-heparin plasma. Regarding the acceptance criteria, the slope of each matrix comparison fell within the set range, and each $R^2$-value exceeded 0.95. Together, these results show that samples of serum, EDTA plasma, and Li-heparin plasma are viable for use in the automated immunoassay described herein.

Interference

Interference studies were performed to evaluate the effect of potentially interfering endogenous and exogenous substances on the performance and outcome of the immunoassay. Three confirmed negative samples, three positive samples with a low level of neutralizing antibody, and three positive samples with a high level of neutralizing antibody were tested in conjunction with each potential interferent. The study was performed and evaluated according to CLSI EP07, "Interferent Testing in Clinical Chemistry." As a study control, the same samples were also tested in the absence of the potential interferent. Testing of control and interferent-spiked samples was performed in duplicate. For each sample and each interference substance, the recovery of the sample spiked with the interferent was compared to the corresponding control sample spiked with the diluent/buffer of the interferent. This accounted for any dilution or alteration of samples caused by spiking. An acceptable outcome was for no false positive or false negative results to be observed.

The DZ-Lite instrument automatically provided the results in AU/mL and reported them as positive or negative ($\geq 1$ AU/mL=Positive; <1 AU/mL=Negative). The substances shown below, at the tolerance levels indicated in Table 3, were not found to significantly interfere with the immunoassay.

TABLE 3

Potentially interfering substance and immunoassay tolerance level

| Substance | Tolerance Level |
| --- | --- |
| Free bilirubin | 40 mg/dL |
| Conjugated bilirubin | 40 mg/dL |
| Hemoglobin | 500 mg/dL |
| Total protein | 12.0 g/dL |
| Triglycerides | 1000 mg/dL |
| Creatinine | 30 mg/dL |
| Rheumatoid Factor | 200 IU/mL |
| Acetaminophen | 20.0 mg/dL |
| Acetylsalicylic Acid | 60.0 mg/dL |
| Ampicillin | 5.3 mg/dL |
| Ascorbic Acid | 176 mg/dL |
| Biotin | 100.0 ng/mL |
| Ethanol | 400.0 mg/dL |
| Heparin | 3.0 U/mL |
| Ibuprofen | 50.0 mg/dL |
| Vancomycin | 10.0 mg/dL |

Cross-Reactivity

Unexpected reactivity can lead to a false positive result. Thus, experiments were performed to determine whether the neutralizing antibody assay produced a positive result from exposure to antibodies of infectious agents other than SARS-CoV-2. Native serum samples (non-spiked) obtained from patients confirmed positive for antibodies to various infectious diseases were evaluated in an open-label study. A minimum of five individual antibody-positive serum samples were evaluated for each infectious disease. EP7-02: Interference Testing in clinical Chemistry Evaluation; Approved Principle-Second Edition was used as a reference standard.

Serum samples having antinuclear antibodies (ANA) or antibodies to *Haemophilus influenzae*, hepatitis B virus, hepatitis C virus, human coronavirus 229E (alpha coronavirus), human coronavirus HKU1 (beta coronavirus), human coronavirus NL63 (alpha coronavirus), human coronavirus OC43 (beta coronavirus), human immunodeficiency virus (HIV), influenza A virus, influenza B virus, parainfluenza virus, and respiratory syncytial virus were tested in cross-reactivity studies. In some cases, as many as ten samples of a particular specimen were tested. As noted, the instrument operator had no role in determining the results of the study. The analyzer automatically provides the results in AU/mL and reports them as positive or negative, using the cut-off of 1 AU/mL. A positive result was not produced at any point during the study, indicating the absence of cross-reactivity.

Reference Range

The reference range of the immunoassay was determined by assessing serum samples of SARS-CoV-2 positive and negative individuals. In an IRB-approved study, serum samples from 100 SARS-CoV-2 PCR-negative patients and 108 SARS-CoV-2 PCR-positive patients were subjected to the neutralizing antibody assay described herein. SARS-CoV-2 PCR positive and negative status was established using nasopharyngeal and oropharyngeal swabs and EUA-approved, PCR-based, nucleic acid amplification tests (NAAT): Boston Heart COVID-19 RT-PCR Test. Results of the study were automatically generated by the DZ-Lite instrument. A positive or negative result was determined using a threshold of 1 AU/mL. All samples were collected under IRB protocols, and the study was open-label.

All 100 PCR-determined negative specimens were confirmed negative in the immunoassay (data not shown). Statistical analysis of the data showed that serum samples from SARS-CoV-2 PCR negative patients had a median neutralizing antibody value of 0.30 AU/mL (95% CI: 0.20-0.40 AU/mL). All except one of the 108 PCR-determined positive specimens were confirmed positive in the immunoassay (data not shown). The median neutralizing antibody value was found to be 3.64 AU/mL (95% CI: 2.48-5.82 AU/mL). Samples from PCR negative patients (n=100) has Medium (interquartile range (IQR)) of 0.30 (0.20-0.40), while samples from PCR positive patients (n=108) has Medium (IQR) of 3.64 (2.46-5.82). These results show that the median obtained value and IQR was below 1 AU/mL for SARS-CoV-2 PCR-negative patients and above 1 AU/mL for SARS-CoV-2 PCR-positive patients. Together, these data validate use of 1 AU/mL as a threshold for indicating a positive or negative result.

Clinical Agreement with a Comparator

The aim of this study was to compare the results obtained by the automated chemiluminescent immunoassay described herein to those obtained by a cell-based SARS-CoV-2 Reporter Neutralization Assay (mNG-NT assay) developed by University of Texas Medical Branch (UTMB). The mNG-NT assay was previously validated and found substantially equivalent to the standard plaque reduction assay (PRNT) (Muruato et al., *Nature Communications* 2020;

11:4059). In the mNG-NT assay, a sample is positive if the dilution factor that neutralizes 50% of fluorescent cells ($NT_{50}$) is equal or higher than 20. A sample is negative if the dilution factor that neutralizes 50% of fluorescent cells ($NT_{50}$) is lower than 20. A positive percent agreement (PPA) of 90% or higher and a negative percent agreement (NPA) of 95% or higher would determine acceptable correlation between the two assays.

Serum samples collected retrospectively from RT-PCR positive patients and RT-PCR negative patients were tested with automated neutralizing antibody assay in an open-label study. The SARSCoV-2 PCR positive and negative patients were established using the EUA-approved, PCR-based, nucleic acid amplification tests (NAAT): Abbott ID NOW Isothermal NAAT and Hologic Fusion RT-PCR. Samples were tested on the DZ-Lite instrument in a single replicate. As described, the analyzer reported either a positive or negative, using the cut-off of 1 AU/mL. Instrument operators were not in making a decision about the positivity or negativity of a result.

Concurrently, aliquots of the same serum samples were submitted to UTMB for testing with the cell-based SARS-CoV-2 Reporter Neutralization Assay (mNG-NT assay). Testing was performed using a reporter SARS-COV-2 stable virus engineered to include a fluorescent molecule (mNeon-Green, mNG). Briefly, patient sera were serially diluted and incubated with the reporter virus. After incubation at 37° C. for 1 h, Vero CC-81 cells (pre-seeded in a 96-well plate) were infected with the virus/serum mixtures at a multiplicity of infection (MOI) of 0.5. At 16 h post-infection, the mNG-positive cells were quantitated using a high content imaging reader. The fluorescence of infected cells was quantified to estimate the $NT_{50}$ value for each serum.

After reporter viral infection, the cells turned green in the absence of serum; in contrast, incubation of the reporter virus with SARS-CoV-2 positive patient serum decreased the number of fluorescent cells. A dose-response curve was obtained by plotting the number of fluorescent cells and the fold of serum dilution, which allowed for the determination of the dilution factor that neutralized 50% of fluorescent cells ($NT_{50}$). The dilution factor cutoff of 20 was established and validated: positive $NT_{50}$ of ≥20 and negative $NT_{50}$ of <20 (Muruato et al., *Nature Communications* 2020; 11:4059).

Qualitative Agreement

Qualitative agreement between the two assays was determined with using 33 retrospectively collected RT-PCR positive samples and 50 retrospectively collected RT-PCR negative samples. Results were used to calculated Positive Percent Agreement (PPA) and Negative Percent Agreement (NPA). The results of each assay were in agreement for every positive and every negative sample (data not shown). Table 4 shows statistical analysis of the obtained results.

TABLE 4

Qualitative Agreement of Neutralizing Antibody Assays

|  |  | Cell-based SARS-CoV-2 Neutralizing Antibodies Assay (UTMB) | |
| --- | --- | --- | --- |
|  |  | Positive (n = 33) | Negative (n = 50) |
| Automated SARS-CoV-2 Neutralizing Antibody Assay | Positive | 33 | 0 |
|  | Negative | 0 | 50 |
|  | Agreement (%) | PPA: 100% (95% CI 89.6-100.0%) | NPA: 100% (95% CI: 92.9-100.0%) |

Quantitative Agreement

In a quantitative comparison, the amount of neutralizing antibody (in AU/mL as measured by the automated immunoassay) needed to generate almost complete inhibition of viral infection in the UTMB cell-based mNG-NT assay was assessed by testing 30 positive patient serum samples (measuring between 2.6 and 22.6 AU/mL) with the mNG-NT assay. It was determined that 2.6 AU/mL yielded nearly 100% inhibition of viral infection in the UTMB assay (data not shown).

Figure 6:
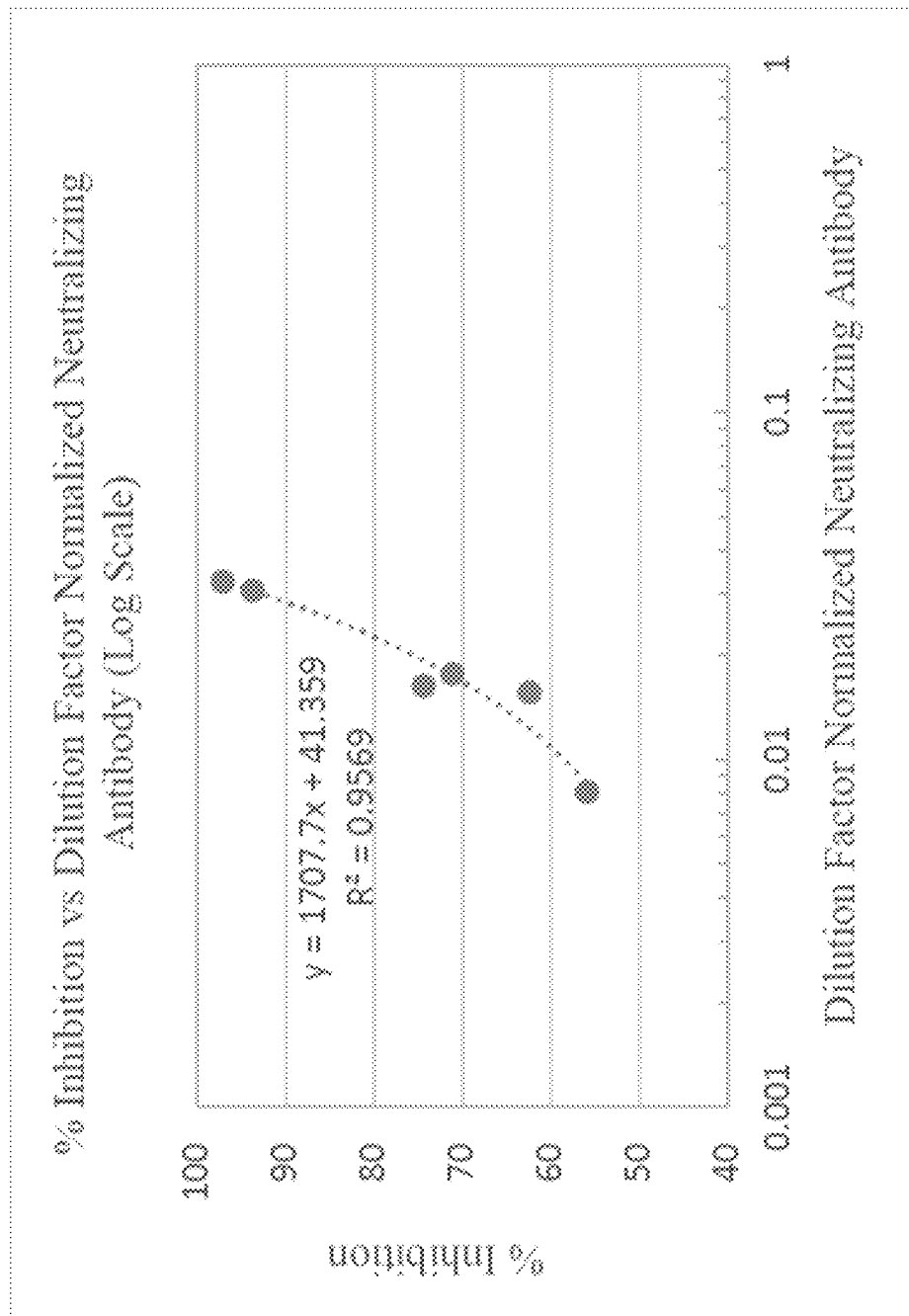
FIG. 6 shows a plot of the percentage inhibition (%) of cell entry of the reporter SARS-CoV-2 virus versus the dilution factor-normalized neutralizing antibody values (AU/mL) in samples.

In another study, six serum samples positive for neutralizing antibodies, as confirmed by the immunoassay, were tested in parallel with the mNG-NT assay. These samples (ranging between 2.6 AU/mL to 22.6 AU/mL) were diluted at different dilution factors and tested with the cell-based mNG-NT assay to measure the percentage inhibition (%) of cell entry of the reporter SARS-CoV-2 virus. FIG. 6 shows a plot of the percent inhibition of cell entry versus the dilution factor-normalized neutralizing antibody values (AU/mL) in samples. As expected, percent inhibition and normalized neutralizing antibody levels were directly related. The greater the neutralizing antibody level, the greater the percentage of inhibition.

Figure 7:
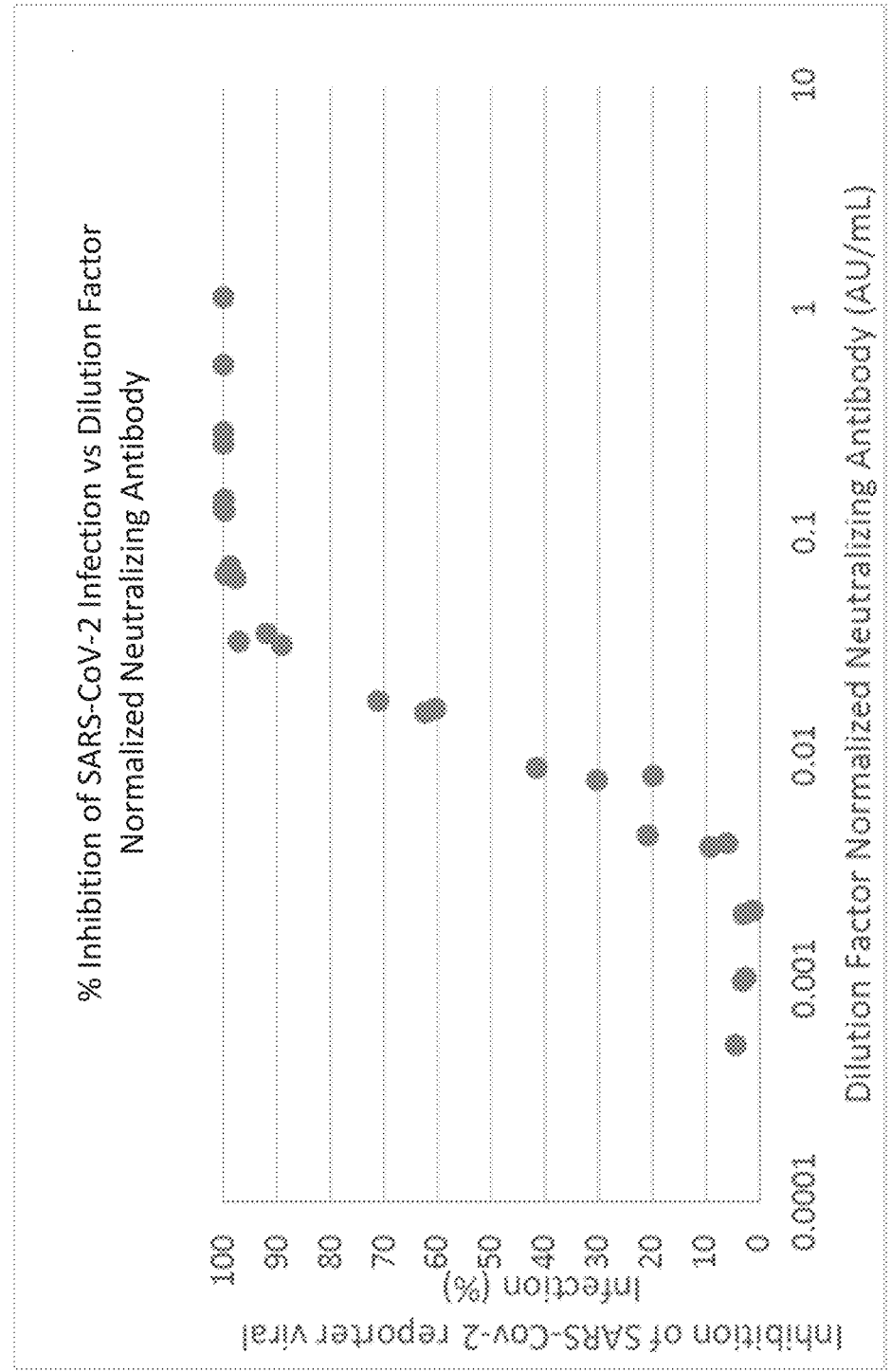
FIG. 7 shows a plot of the inhibition of SARS-CoV-2 reporter viral infection (%) of three serum samples positive for SARS-CoV-2 neutralizing antibodies versus the dilution factor normalized neutralizing antibody (AU/mL), as measured by an exemplary automated immunoassay disclosed herein.
Figure 8:
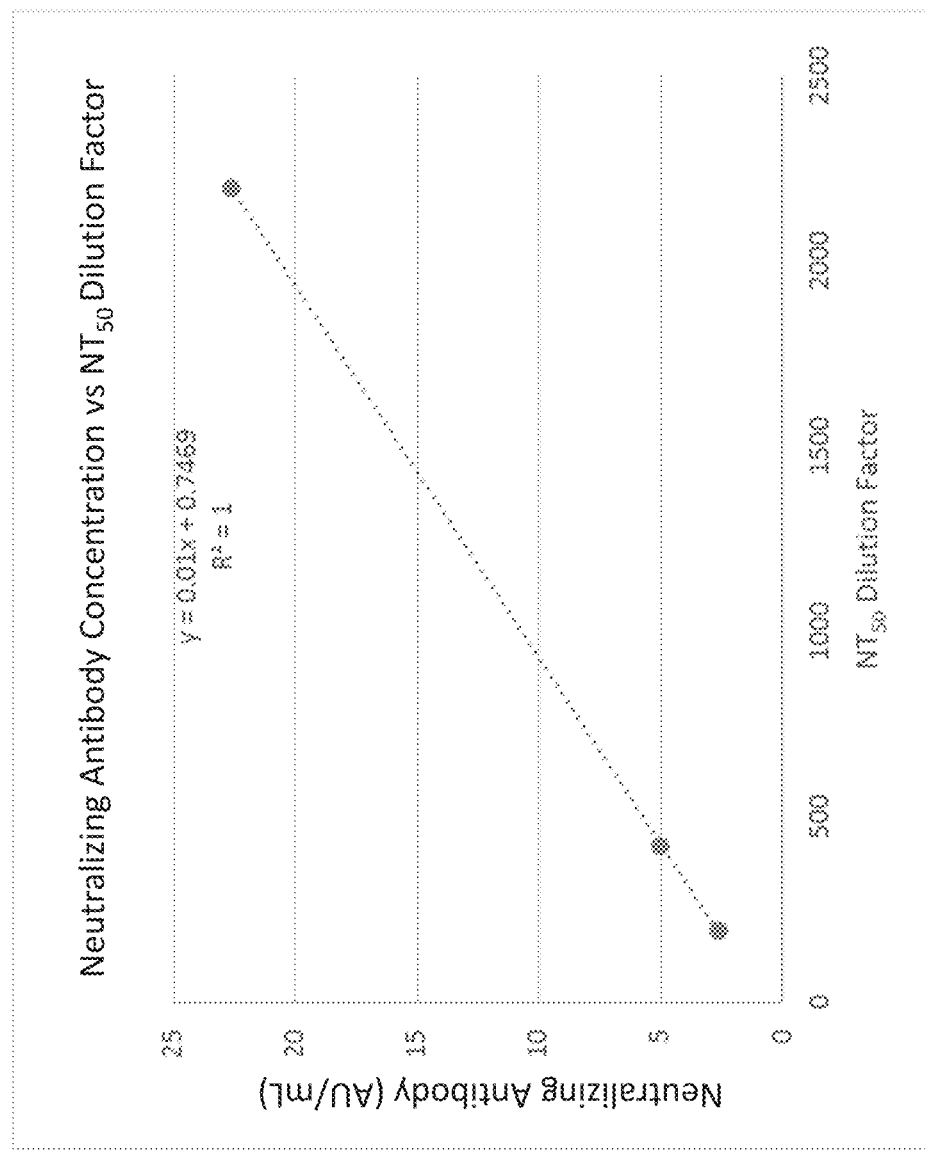
FIG. 8 shows a plot of the $NT_{50}$ of the same samples as FIG. 7, as determined by the cell-based SARS-CoV-2 Reporter Neutralization Assay (mNG-NT assay), against the AU/mL for SARS-CoV-2 neutralizing antibody determined by the exemplary automated immunoassay disclosed herein.

In a final comparison, three serum samples positive for neutralizing antibodies, as determined by the automated immunoassay (measuring 2.6 AU/mL, 5.0 AU/mL, and 22.6 AU/mL, respectively), were serially diluted 20- to 5120-fold, and their corresponding inhibitions of viral infection (%) were measured by the cell-based mNG-NT assay. FIG. 7 shows a plot of inhibition of SARS-CoV-2 reporter viral infection (%) versus the dilution factor normalized neutralizing antibody (AU/mL), as measured by the automated assay. The obtained sigmoid-shaped curve shows a clear correlation between the two methods. In fact, using the curve shown in FIG. 7, a measurement of the neutralizing antibody concentration by the automated immunoassay can be used to accurately predict the percent inhibition of the reporter viral infection in the cell-based mNG-NT assay. FIG. 8 shows a plot of the $NT_{50}$ of the same undiluted samples, as determined by the cell-based UTMB assay, against the AU/mL determined by the automated immunoassay (2.6 AU/mL, 5.0 AU/mL, and 22.6 AU/mL) disclosed herein. The plot shows clear correlation between the two methods. Together, these results demonstrate excellent correlation between the automated immunoassay and the cell-based SARS-CoV-2 Reporter Neutralizing Antibody Assay (mNG-NT assay).

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

The invention claimed is:

1. A method for analyzing a sample, comprising:
   a) contacting the sample with a particle coated with a surface antigen from a coronavirus, and with a receptor for the surface antigen which is labelled with a detectable moiety, wherein the particle is a magnetic particle,
wherein the sample comprises or is suspected of comprising an antibody that reduces or inhibits binding between the surface antigen and the receptor,
wherein labelled receptors that specifically bind to the surface antigen are immobilized on the particle via the surface antigen, wherein the antibody, if present in the sample, competes with or displaces one or more of the labelled receptors,
b) precipitating the particle in a magnetic field,
c) decanting supernatant and washing the particle, and
d) detecting a signal associated with the detectable moiety of labelled receptors that remain immobilized on the particle, and a magnitude of the signal is inversely proportional to an amount or level of the antibody in the sample.

2. The method of claim 1, wherein the receptor for the surface antigen is in a solution.

3. The method of claim 1, wherein the sample is a serum or plasma sample.

4. The method of claim 1, wherein the surface antigen is a spike (S) protein or fragment, domain, subunit, or variant thereof.

5. The method of claim 4, wherein the surface antigen is a receptor binding domain (RBD) of a SARS-CoV-2 or fragment thereof, and wherein the receptor is a human ACE2 or functional fragment, domain, or subunit thereof.

6. The method of claim 1, wherein the detectable moiety is a chemiluminescent signal generating molecule or complex, wherein the detectable moiety is selected from the group consisting of Acridinium Ester (AE), N-(4-aminobutyl)-N-ethylisoluminol (ABEI), Alkaline Phosphatase (AP), and Horseradish Peroxidase (HRP).

7. The method of claim 1, wherein the antibody is a neutralizing antibody to the coronavirus.

8. The method of claim 7, wherein the neutralizing antibody specifically recognizes a receptor binding domain (RBD) of a SARS-CoV-2 or fragment thereof.

9. The method of claim 1, wherein the sample is from a subject having, suspected of having, or having recovered from a SARS-CoV-2 infection.

10. The method of claim 1, wherein the sample is from a subject having received a prophylactic and/or therapeutic intervention for a SARS-CoV-2 infection, wherein the intervention comprises vaccination, passive immunization, or administering a monoclonal or polyclonal antibody to the subject.

11. The method of claim 1, further comprising:
contacting a calibrator sample and/or a control sample with the particle, and with the receptor which is labelled with the detectable moiety,
wherein the calibrator sample comprises a high or low concentration of a SARS-CoV-2 neutralizing antibody, and the control sample comprises a known concentration of a SARS-CoV-2 neutralizing antibody.

12. The method of claim 11, wherein the calibrator sample comprises a first calibrator sample comprising a high concentration of the SARS-CoV-2 neutralizing antibody and a second calibrator sample comprising a low concentration of the SARS-CoV-2 neutralizing antibody.

13. The method of claim 11, wherein the control sample comprises a plurality of control samples comprising known concentrations of the SARS-CoV-2 neutralizing antibody.

14. The method of claim 11, wherein the calibrator samples and/or the control sample is pooled serum.

* * * * *

UNITED STATES PATENT AND TRADEMARK OFFICE
CERTIFICATE OF CORRECTION

| | | |
|---|---|---|
| PATENT NO. | : 12,044,686 B2 | Page 1 of 1 |
| APPLICATION NO. | : 17/376058 | |
| DATED | : July 23, 2024 | |
| INVENTOR(S) | : Chong-Sheng Yuan et al. | |

It is certified that error appears in the above-identified patent and that said Letters Patent is hereby corrected as shown below:

In the Specification

Column 9-10 (TABLE 1A-continued), Line 39 (Approx.), delete "EPIvISL_408481" and insert -- EPI_ISL_408481 --.

Column 9-10 (TABLE 1A-continued), Line 59 (Approx.), delete "168 BetaCov/Jiangsu/S01/2020" and insert -- 168 BetaCov/Jiangsu/JS01/2020 --.

Column 11-12 (TABLE 1A-continued), Line 29 (Approx.), delete "80 BetaCovaapan/KY-V-029/2020" and insert -- 80 BetaCov/Japan/KY-V-029/2020 --.

Column 15, Line 1, delete "4400-402" and insert -- Δ400-402 --.

Column 15, Line 3, delete "469-70" and insert -- Δ69-70 --.

Column 17, Line 51, delete ""VHH." A VHH" and insert -- "$V_HH$." A $V_HH$ --.

Signed and Sealed this
Tenth Day of February, 2026

John A. Squires
*Director of the United States Patent and Trademark Office*